(12) United States Patent
Kruper et al.

(10) Patent No.: US 8,304,563 B2
(45) Date of Patent: *Nov. 6, 2012

(54) BATCH, SEMI-CONTINUOUS OR CONTINUOUS HYDROCHLORINATION OF GLYCERIN WITH REDUCED VOLATILE CHLORINATED HYDROCARBON BY-PRODUCTS AND CHLOROACETONE LEVELS

(75) Inventors: William J. Kruper, Sanford, MI (US); Tina Arrowood, Coleman, MI (US); Bruce M. Bell, Higgins Lake, MI (US); John Briggs, Midland, MI (US); Robert M. Campbell, Midland, MI (US); Bruce D. Hook, Lake Jackson, TX (US); Anh Nguyen, Lake Jackson, TX (US); Curt Theriault, Hemlock, MI (US); Ralf Fitschen, Stade (DE)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/017,645

(22) Filed: Jan. 31, 2011

(65) Prior Publication Data

US 2011/0124890 A1 May 26, 2011

Related U.S. Application Data

(60) Division of application No. 11/710,002, filed on Feb. 22, 2007, now Pat. No. 7,906,690, which is a continuation-in-part of application No. 11/628,269, filed as application No. PCT/US2005/025443 on Jul. 18, 2005, now Pat. No. 8,088,957.

(60) Provisional application No. 60/589,683, filed on Jul. 21, 2004.

(51) Int. Cl.
*C07D 301/24* (2006.01)

(52) U.S. Cl. .................................................. 549/521
(58) Field of Classification Search .................. 549/521
See application file for complete search history.

(56) References Cited

U.S. PATENT DOCUMENTS 2,144,612 A    1/1939   Britton et al.
(Continued)

FOREIGN PATENT DOCUMENTS

DE        197308        4/1908
(Continued)

OTHER PUBLICATIONS

Gibson, G.P., Chemistry and Industry, The Preparation, Properties, and Uses of Glycerol Derivatives. Part III. The Chlorohydrins, 1931, 20, 949-975.
Conant, J.B., et al., Organic Synthesis CV 1, Methods of Preparation, 292-296, 1941.

(Continued)

*Primary Examiner* — Taylor Victor Oh

(57) ABSTRACT

The present invention relates to a process for converting a multihydroxylated-aliphatic hydrocarbon or ester thereof to a chlorohydrin, by contacting the multihydroxylated-aliphatic hydrocarbon or ester thereof starting material with a source of hydrogen chloride at superatmospheric, atmospheric and subatmospheric pressure conditions for a sufficient time and at a sufficient temperature, preferably wherein such contracting step is carried out without substantial removal of water, to produce the desired chlorohydrin product; wherein the desired product or products can be made in high yield without substantial formation of undesired overchlorinated byproducts; said process carried out without a step undertaken to specifically remove volatile chlorinated hydrocarbon by-products or chloroacetone, wherein the combined concentration of volatile chlorinated hydrocarbon by-products and chloroacetone is less than 2000 ppm throughout any stage of the said process.

42 Claims, 4 Drawing Sheets

U.S. PATENT DOCUMENTS

| | | | |
|---|---|---|---|
| 5,908,946 A | 6/1999 | Stern et al. | |
| 6,288,248 B1 | 9/2001 | Strebelle et al. | |
| 7,151,187 B2 | 12/2006 | Delfort et al. | |
| 7,906,691 B2 | 3/2011 | Krafft et al. | |
| 2011/0178315 A1* | 7/2011 | Hook et al. | 549/521 |

FOREIGN PATENT DOCUMENTS

| | | |
|---|---|---|
| DE | 1075103 | 2/1960 |
| WO | 9514635 | 6/1995 |
| WO | 02092586 A1 | 11/2002 |
| WO | 2005021476 A1 | 3/2005 |
| WO | 2005054167 A1 | 6/2005 |

OTHER PUBLICATIONS

Carre, Mauclere, C.R. Hebd. Seances Acad, Sci., 1931, 192, 1567-9.
Gomez, et al., Tetrahedron Letters 2000, 41, 6049-6052.
Leadbeater, et al., Tetrahedron 2003, 59, 2253-58.
Viswanathan, et al., Current Science, 1978, 21, 802-803.
Breslow, R., Organic Reaction Mechanisms, 2nd Edition W.A. Benjamim, Inc., Menlo Park, CA, 1964, pp. 83-84.
Paizs, C., et al., Journal of the Chemical Society, Perkin Transactions I, 2002, 21, 2400-2402.
Levene, et al., Organic Synthesis, Collective vol. 2, Ed., H.A. Blatt; John Wiley and Sons Inc., New York, 1943, pp. 5-6.

* cited by examiner

BATCH, SEMI-CONTINUOUS OR CONTINUOUS HYDROCHLORINATION OF GLYCERIN WITH REDUCED VOLATILE CHLORINATED HYDROCARBON BY-PRODUCTS AND CHLOROACETONE LEVELS

CROSS REFERENCE TO RELATED APPLICATIONS

This application is a divisional of co-pending application Ser. No. 11/710,002 filed Feb. 22, 2007, which is a continuation-in-part of application Ser. No. 11/628,269, filed Jul. 18, 2005, which claims the benefit of U.S. application Ser. No. 11/628,269 (PCT/US05/025443), filed Jul. 18, 2005, which claims the benefit of U.S. Provisional application No. 60/589,683, filed Jul. 21, 2004.

BACKGROUND OF THE INVENTION

The present invention relates to a batch, semi-batch, continuous or semi-continuous process for converting a multihydroxylated-aliphatic hydrocarbon or an ester thereof to a chlorohydrin. More specifically, the present invention relates to a process wherein the multihydroxylated-aliphatic hydrocarbon or an ester thereof is a glycerol; and the chlorohydrin is a dichlorohydrin and an ester thereof, for example, 1,3-dichloro-2-propanol and/or 2,3-dichloro-1-propanol (DCH isomers). The process of the present invention has a benefit of producing chlorohydrins having a low concentration of volatile, by-product of halogenated hydrocarbon including chloroacetone. Chlorohydrins prepared by the process of the present invention, are useful in preparing epoxides such as epichlorohydrins. Unexpectedly, compositions of chlorohydrins and dichlorohydrins of glycerol have been found to have combined concentrations of volatile chlorinated hydrocarbon by-products and chloroacetone less than 2000 ppm throughout any stage of the said process.

Epichlorohydrin is a widely used precursor to epoxy resins. Epichlorohydrin is a monomer which is commonly used for the alkylation of para-bisphenol A; the resultant diepoxide, either as a free monomer or oligomeric diepoxide, may be advanced to high molecular weight resins which are used for example in electrical laminates, can coatings, automotive topcoats and clearcoats.

A known process for the manufacture of epichlorohydrin involves hypochlorination of allyl chloride to form dichlorohydrin. Ring closure of the dichlorohydrin mixture with caustic affords epichlorohydrin which is distilled to high purity (>99.6%). This chlorohydrin process requires two equivalents of chlorine and one equivalent of caustic per molecule of epichlorohydrin.

In another known process for producing epichlorohydrin the first step involves installing oxygen in the allylic position of propylene, via a palladium catalyzed reaction of molecular oxygen in acetic acid. The resulting allyl acetate is then hydrolyzed, chlorinated and the incipient dichlorohydrin is ring closed with caustic to epichlorohydrin. This process avoids the production of allyl chloride and therefore uses less chlorine (only one equivalent).

Both known processes for the manufacture of epichlorohydrin described above require the sacrificial use of chlorine, and complications associated with the industrial use and generation of hypochlorous acid (HOCl) can be magnified at industrial scale and these processes are known to produce substantial amounts of chlorinated by-products. In particular, it is well known that the hypochlorination of allyl chloride produces 1,2,3-trichloropropane and other undesirable chlorinated ethers and oligomers (RCls). RCl issues are managed as an increased cost to manufacture. As new capital is added to accommodate greater global production, a substantial investment in downstream processing must be added to accommodate and remediate these unwanted by-products. These same problems are analogous in the HOCl routes to propylene and ethylene chlorohydrin, and thus, these routes are less practiced.

An alternative process, which avoids the generation of HOCl, for example as described in WO 2002092586 and U.S. Pat. No. 6,288,248 involves the direct epoxidation of allyl chloride using titanium silicalite catalysis with hydrogen peroxide. Despite the advantage of reducing the generation of HOCl, allyl chloride is still an intermediate. The disadvantage of using allyl chloride is two-fold: (1) The free radical chlorination of propylene to allyl chloride is not very selective and a sizable fraction (>15 mole %) of 1,2-dichloropropane is produced. (2) Propylene is a hydrocarbon feedstock and long-term, global forecast of propylene price continues to escalate. A new, economically viable process for the production of epichlorohydrin which avoids the complications of controlled, chlorine-based oxidation chemistry and RCl generation is desirable. There is a need in the industry for a process for the generation of epichlorohydrin which involves a non-hydrocarbon, renewable feedstock.

Glycerin is considered to be a low-cost, renewable feedstock which is a co-product of the biodiesel process for making fuel additives. It is known that other renewable feedstocks such as fructose, glucose and sorbitol can be hydrogenolized to produce mixtures of vicinal diols and triols, such as glycerin, ethylene glycol, 1,2-propylene glycol, 1,3-propylene glycol and the like.

With abundant and low cost glycerin or mixed glycols, an economically attractive process for glycerin or mixed glycol hydrochlorination would be desirable. It would be advantageous if such a process were highly chemoselective to the formation of vicinal chlorohydrins, without production of RCls.

A process is known for the conversion of glycerol (also referred to herein as "glycerin") to mixtures of dichloropropanols (also referred to herein as "dichlorohydrins" or DCH), compounds I and II, as shown in Scheme 1 below. The reaction is carried out in the presence of anhydrous HCl and an acetic acid (HOAc) catalyst with water removal. Both compounds I and II can then be converted to epichlorohydrin via treatment with caustic.

Scheme 1: Hydrochlorination of Glyerol

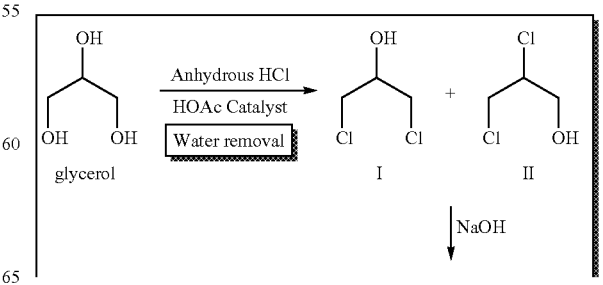

-continued

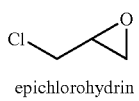
epichlorohydrin

Various processes using the above chemistry in Scheme 1 have been reported in the prior art. For example, epichlorohydrin can be prepared by reacting a dichloropropanol such as 2,3-dichloropropan-1-ol or 1,3-dichloropropan-2-ol with base. Dichloropropanol, in turn, can be prepared at atmospheric pressure from glycerol, anhydrous hydrochloric acid, and an acid catalyst. A large excess of hydrogen chloride (HCl) gas is recommended to promote the azeotropic removal of water that is formed during the course of the reaction.

For example, Gibson, G. P., *Chemistry and Industry* 1931, 20, 949-975; and Conant et al., *Organic Synthesis CV* 1, 292-294, and *Organic Synthesis CV* 1, 295-297; have reported distilled yields of dichlorohydrins in excess of 70% for dichlorohydrins, compounds I and II in Scheme 1 above, by purging a large excess of anhydrous HCl (up to 7 equivalents) through a stirred solution of glycerol and an organic acid catalyst. The processes described in the above references require the use of atmospheric pressures of HCl which is used as an azeotroping agent to remove the accumulated water. Other azeotropes are known. For example, U.S. Pat. No. 2,144,612 describes using n-butyl ether along with excess hydrogen chloride (HCl) gas to promote the reactive distillation and removal of water.

Indeed, all of the prior art teaches the vaporization of azeotropes with water to provide high conversion and a process need for sub-atmospheric or atmospheric pressure conditions to accomplish water removal. U.S. Pat. No. 2,144,612 argues the advantageous use of an added azeotroping agent (for example, n-butyl ether) to promote the reactive azeotropic distillation and elimination of water, again using excess HCl at atmospheric conditions. A similar approach using vacuum removal of water is taught in German Patent No. 1075103.

German Patent No. 197308 teaches a process for preparing a chlorohydrin by the catalytic hydrochlorination of glycerine by means of anhydrous hydrogen chloride. This reference teaches a batch process with separation of water at atmospheric conditions. German Patent No. 197308 does not teach carrying out the hydrochlorination reation process at elevated pressures.

All known prior art for the production of chlorohydrin reports hydrochlorination processes where water is removed as a co-product from the process. In particular, WO 2005/021476 teaches a series of hydrochlorination reactions in which the water of reaction is removed in an atmospheric or sub-atmospheric process by reactive distillation. Similar art is taught in WO2005/054167 with the additional teaching that the reaction carried out under higher total pressures (HCl partial pressure not specified) may improve the rate of reaction. However, nothing in WO2005/054167 discloses the use of HCl partial pressure and its effect in its process. WO2005/054167 also exemplifies the need to remove water to effect high conversion and selectivity under atmospheric or subatmospheric pressures. Neither WO 2005/021476 nor WO2005/054167 teaches any advantage of leaving water in their processes, or that removing the water effects the formation of unwanted chloroethers and RCl's. RCl's are halogenated hydrocarbon by-products of either a volatile or high boiling nature.

The use of extremely large excess amounts of hydrogen chloride (HCl) gas is economically problematic and the inherent contamination with water of the unreacted hydrogen chloride and RCl's results in an aqueous hydrogen chloride stream that is not easily recyclable. Furthermore, reaction times of 24 to 48 hours are required to achieve a far from complete conversion of glycerin; however, the products often include significant amounts of the undesired overchlorinated trichloropropane and chlorinated ethers. Other processes are also known that use reagents that convert alcohols to chlorides but that scavenge water in situ. For example, thionyl chloride can be used to convert glycerin to a chlorohydrin, as described in Cane, Mauclere C. R. *Hebd. Seances Acad. Sci.* 1930, 192 and may be selective, but produces stoichiometric amounts of $SO_2$. The cost and expense of this reagent is not acceptable for the industrial production of epichlorohydrin or any other chlorohydrin derived from a multihydroxylated-aliphatic hydrocarbon. Likewise, other hydrochlorination reagents which are mild and effective are considered expensive and exotic for this transformation, as described in Gomez, et al. *Tetrahedron Letters* 2000, 41, 6049-6052. Other low temperature processes convert the alcohol to a better leaving group (for example, mesylate) and provide a soluble form of chloride via an ionic liquid used in molar excess, as described in Leadbeater, et al. *Tetrahedron* 2003, 59, 2253-58. Again, the need for anhydrous conditions, stoichiometric reagents and an expensive form of chloride prevents industrial consideration of the above process. Furthermore, these reagents can cause exhaustive chlorination of a multihydroxylated-aliphatic hydrocarbon, leading again to undesirable RCl by-products, as taught in Viswanathan, et al. *Current Science,* 1978, 21, 802-803.

To summarize, there are at least five major disadvantages to all of the above known approaches for preparing a chlorohydrin from glycerin or any other vicinal-diol, triol or multihydroxylated-aliphatic hydrocarbon: (1) Atmospheric pressure processes for the hydrochlorination of glycerin or any diol require a large excess of HCl, oftentimes 7-10 fold molar excess. In an atmospheric pressure process the excess anhydrous HCl is then contaminated with water. (2) Variants of the above known processes are very slow, batch type reactions, which often take between 24-48 hours at temperatures in excess of 100° C. and do not exceed 80-90% conversion to desired chlorohydrin product(s). (3) Exotic hydrochlorination reagents may drive the reaction by scavenging water, but oftentimes produce a by-product inconsistent with the economic production of a commodity. (4) All of the above approaches produce higher levels of unwanted RCls, as defined above for glycerin hydrochlorination. (5) When the reaction is run at elevated pressure to control evaporation of the reactor contents, low partial pressures of HCl result in low conversions or retarded reaction rates.

The prior art concludes that water removal is required to promote complete conversion of glycerin to dichlorohydrins. To accommodate this water removal requirement, the prior art reactions are conducted under azeotropic or reactive distillation or extraction conditions which requires a co-solvent or chaser and considerable capital addition to the process. All prior art has concluded that there is an equilibrium limitation to this conversion due to the presence of water in the reaction mixture.

It is desired in the industry to provide a hydrochlorination process for the production of high purity chlorohydrins from multihydroxylated-aliphatic hydrocarbons which overcome all of the inadequacies of the prior art. It would, therefore, be an advance in the art of chlorohydrin chemistry to discover a simple and cost-effective method of transforming diols and triols to chlorohydrins.

SUMMARY OF THE INVENTION

One aspect of the present invention is directed to a batch, semi-batch, semi-continuous or continuous process for producing a chlorohydrin, an ester of a chlorohydrin, or a mixture thereof comprising the step of contacting glycerin, an ester of glycerin, or a mixture thereof with a source of hydrogen chloride, in the presence of a catalyst to produce a chlorohydrin, an ester of a chlorohydrin, or a mixture thereof, said process carried out without a step undertaken to specifically remove volatile chlorinated hydrocarbon by-products or chloroacetone, wherein the combined concentration of volatile chlorinated hydrocarbon by-products and chloroacetone is less than 2000 ppm throughout any stage of the said process.

One embodiment of the present invention is directed to a batch, semi-batch, continuous or semicontinuous process for producing a chlorohydrin, an ester of a chlorohydrin, or a mixture thereof comprising the step of contacting a multihydroxylated-aliphatic hydrocarbon, an ester of a multihydroxylated-aliphatic hydrocarbon, or a mixture thereof with a source of a superatmospheric partial pressure of hydrogen chloride to produce a chlorohydrin, an ester of a chlorohydrin, or a mixture thereof without substantially removing water. "Superatmospheric pressure" herein means that the hydrogen chloride (HCl) partial pressure is above atmospheric pressure, i.e. 15 psia or greater and this operative pressure preferably occurs within the confines of the convertor or reactor. The elements of this invention are especially applicable when the multihydroxylated hydrocarbon is glycerin.

It is an objective of the present invention to further minimize the formation of unwanted RCl's or chlorinated glycerol oligomers using the process of the present invention.

Another embodiment of the present invention uses hydrogen chloride gas as the hydrogen chloride source to produce a chlorohydrin.

Yet another embodiment of the present invention relates to a batch, semi-batch, continuous or semi-continuous process for preparing a chlorohydrin comprising the step of contacting together at a superatmospheric partial pressure of HCl, for example in the range of from about 20 psia to about 1000 psia; and at a sufficient temperature, for example in the range of from about 25° C. to about 300° C.: (a) a multihydroxylated-aliphatic hydrocarbon, for example a 1,2-diol or a 1,2,3-triol; (b) a catalyst that facilitates the conversion of the multihydroxylated-aliphatic hydrocarbon to a chlorohydrin, for example a carboxylic acid, an ester, a lactone, an amide or a lactam; and mixtures thereof; and (c) a hydrogen chloride source, for example hydrogen chloride gas; wherein the process is carried out without substantially removing water during the contacting step.

Still another embodiment of the present invention relates to a batch, semi-batch, continuous or semi-continuous process for preparing a dichlorohydrin of glycerin comprising the step of contacting together at a superatmospheric partial pressure of HCl, for example in the range of from about 20 psia to about 1000 psia; and at a sufficient temperature, for example in the range of from about 25° C. to about 300° C.: (a) an ester of a multihydroxylated-aliphatic hydrocarbon, for example glycerin monoacetate; and (b) a hydrogen chloride source, for example hydrogen chloride; wherein the process is carried out without substantially removing water during the contacting or reaction step.

Still another embodiment of the present invention is directed to the advantages of a superatmospheric pressure hydrochlorination of a multi-hydroxylated hydrocarbon process wherein the coproduct water is allowed to remain in the reaction medium.

Another aspect of the present invention is directed to a novel composition which is produced by the aforementioned processes. In particular, the composition of the present batch, semi-batch, continuous or semi-continuous superatmospheric pressure process when applied to glycerin, produces a crude dichlorohydrin which contains low levels of unwanted RCl's. The optional use of a co-catalyst or co-reactant containing a non-volatile source of chloride throughout the process may further improve the quality of the crude or refined dichlorohydrin products.

Advantages of the present invention includes: (1) The present invention process is simplified in that water removal is not required and a co-solvent/chaser is not required. A "superatmospheric pressure process" herein means a process where reaction occurs under the conditions that the hydrogen chloride (HCl) partial pressure is above atmospheric pressure, i.e. 15 psia or greater. The present invention process may be run without additional additives, such as azeotroping agents. (2) The catalyst/HCl partial pressure/temperature range used in the process of the present invention without water removal accelerates the conversion rate of a multihydroxylated-aliphatic hydrocarbon to a chlorohydrin by almost 20-fold. The prior art militated away from using a superatmospheric HCl partial pressure, due to the need by the prior art processes for water removal. (3) Unexpectedly, water allowed to accumulate in a high pressure reaction mixture allows for higher rate of conversion with a higher selectivity process than the prior art, viz, less chlorinated ethers, less RCls are formed in the present invention process than in the prior art atmospheric HCl process. (4) The catalysts used in the present invention process exhibit improvements over other catalysts used in the prior art such as acetic acid, thereby driving selectivity higher and increasing the rate of the process. (5) The superatmospheric pressure process of the present invention uses far less HCl than the atmospheric pressure process of the prior art to achieve even more conversion (for example, 1-25% HCl excess for the present invention versus a 700-1400% excess for the prior art).

The present invention provides new and unexpected benefits by carrying out the batch, semi-batch, continuous or semicontinuous process including for example: (1) High RCl levels known heretofore have been lowered by use of a batch, semi-batch, semi-continuous or continuous process wherein accumulated water co-product is allowed to remain in contact with dichlorohydrin isomers produced from the superatmospheric hydrochlorination of glycerin at high conversion levels of glycerin and monochlorohydrin isomers (MCH). (2) Upon removal of HCl in a distillation stage for the retrieval of dichlorohydrin isomers, the acidic water coproduct retained in the distillation kettle actually lowers the formation of RCl's, including chloroacetone and chlorinated ethers of glycerin. (3) The optional use in a distillation unit of a non-volatile co-catalyst or co-reactant such as NaCl, KCl or an ionic liquid containing non-volatile chloride as counterion further prevents the formation of RCl impurities, including especially chlorinated ethers. (4) The optional use in a continuous or batch reactor train of a non-volatile co-catalyst or co-reactant such as NaCl, KCl or an ionic liquid containing non-volatile chloride as counterion further prevents the formation of RCl impurities, including especially chlorinated ethers.

Another advantaged feature of the hydrochlorination of an multihydroxylated hydrocarbon under superatmospheric conditions without substantial water removal relates to the lowering of other unwanted by-products as well. In the case of glycerin, heretofore, it is known that long reaction times with a standard azeotropic removal of water can produce high levels of chloroacetone. It is also taught in the prior art that at least one removal step is required to lower these unacceptably high levels of chloroacetone. The inherent toxicity of chloroacetone as well as its potential to act as a chain terminator in subsequent reaction of epichlorohydrin with bisphenol-A renders it highly undesirable. It may be expected that a process which attempted to remove water during the hydrochlorination process would provide conditions for the dehydration of 3-chloro-1,2-propanediol (1-MCH). Not to be bound by theory, it is also possible that chloroacetone evolves from the thermal elimination of HCl from 1,3-dichloro-2-propanol.

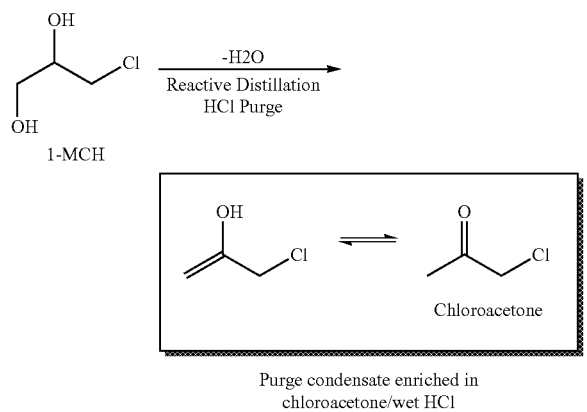

Reactive distillation of water from a medium which contains 1-MCH would further contaminate a wet HCl evolving from the reactor with chloroacetone. This effluent or recycle HCl would be contaminated with low boiling chloroacetone, requiring the need for such chloroacetone to be condensed or removed in a subsequent step before this HCl could be back-added to another hydrochlorination process. Other volatile RCl's such as dichloropropenes and trichloropropene can be concentrated in this purge stream of HCl. It would therefore be of interest and advantage to have never produced substantial quantities of chloroacetone or other halogenated hydrocarbon impurity in any process, particularly in an industrial scale process.

As a matter of course, it is well appreciated in the literature that chloroacetone is an extremely reactive electrophile. For example, it is 33,000 times more reactive toward iodide displacement than is 1-chloropropane (R. Breslow in "Organic Reaction Mechanisms" $2^{nd}$ Edition, W. A. Benjamin Inc., Menlo Park, Calif. 1964, p 83-84. It is further appreciated that chloroacetone is readily hydrolyzed at low temperatures to acetol or hydroxyacetone via enzymic approaches (Paizs, C. et al, *Journal of the Chemical Society, Perkin Transactions* 1 2002, 21, 2400-2402.) as well as with formate or acetate anion (Levene et al in *"Organic Synthesis"* Collective Vol. 2, Ed. H. A. Blatt; John Wiley and Sons Inc., New York, 1943 pp 5-6). In addition, the caustic mediated hydrolysis of chloroacetone is known to be extraordinarily fast and therefore is known under conditions of base-catalyzed epoxidation of a halohydrin (e.g DCH to epichlorohydrin upon sodium hydroxide, saponification treatment). Although removal of chloroacetone during caustic treatment of of DCH is known, it goes without saying that the overall yield of the chlorination process is lowered. In addition, the acetol which is co-produced ends up in the waste water outfall from the said process. It is recognized that acetol in a waste stream imparts toxicity to such outfall and requires further remediation beyond the battery limits of the process. It would be of benefit for an industrial process to minimize acetol or hydroxyacetone in waste water treatment and to never generate sizable amounts of its chloroacetone precursor.

The prior art which operates within the confines of continuous removal of water to ostensibly drive the hydrochlorination process alleges that large quantities of chloroacetone may be produced. In (Gilbeau et al WO 2006, 100311 A3), it is claimed that at least one removal step for the production of DCH is required to lessen the chloroacetone levels. This step may include the saponification process wherein crude dichlorohydrin is reacted with caustic to produce epichlorohydrin. In light of the known facile hydrolysis of this impurity, it is also reported that levels of chloroacetone can be reduced during the saponification of 1-chloro-2-propanol with base (Trent et al WO 95/14635). The reduction of chloroacetone through a caustic treatment is therefore known.

The batch, semi-batch, continuous or semi-continuous superatmospheric pressure process allows the use of crude, wet glycerol as a multihydroxylated-aliphatic hydrocarbon starting material, yet still achieves higher selectivity and faster conversion than prior art without requiring additional water removal.

Another benefit of using the catalysts of the present invention is the simplified process resulting from the use of low volatility, recycleable catalysts, and consequently improved process economics.

The batch, semi-batch, continuous or semi-continuous superatmospheric pressure process of the present invention addresses a need in the art by providing a means for rapidly (for example, less than about 12 hours) converting glycerin or an ester of glycerin to a chlorohydrin in high per-pass yield (for example greater than 90 mole %) and high selectivity (for example, greater than 90 mole %). Surprisingly, the method of the present invention can be carried out without azeotropic or in situ removal of water.

DETAILED DESCRIPTION OF THE INVENTION

Figure 1:
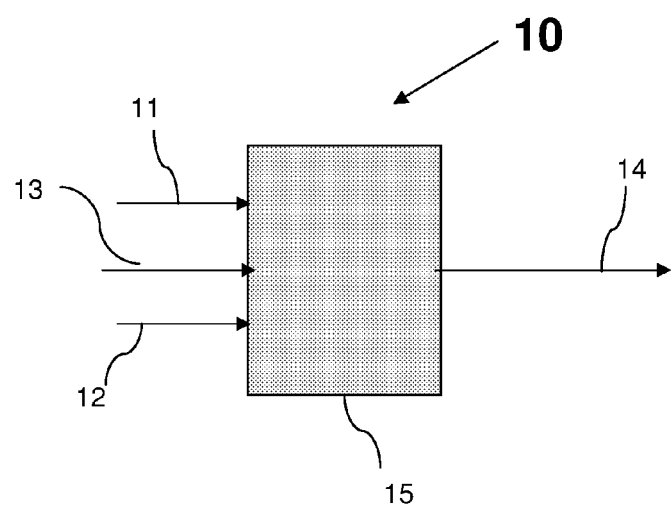
FIG. 1 is a process flowchart illustrating one embodiment of the process of the present invention referred to herein as a once-through, no recycle process.

In one broad aspect of the present invention, the present invention is a process of converting a multihydroxylated-aliphatic hydrocarbon or an ester thereof, such as glycerin or an ester of glycerin, to a chlorohydrin or an ester thereof comprising the step of contacting the glycerin or an ester of glycerin with a hydrogen chloride source at superatmospheric partial pressure and under reaction conditions to produce the chlorohydrin or ester thereof with the substantial absence of water removal. "Substantial absence of water removal" herein means that during the reaction process step or steps, no method is employed to remove the water present in the process (for example, either water of reaction or that introduced with the feed component(s)) during the hydrochlorination step. These methods may include any reactive, cryoscopic, extractive, azeotropic, absorptive or evaporative in-situ or ex-situ techniques or any known techniques for water removal. In a final stage of a batch, semi-batch, continuous or semi-continuous process for the production of dichlorohydrin isomers of glycerin, only then is water and product DCH removed, preferably by distillation or some extractive technique.

The present invention also relates to the process which produces novel compositions of chlorohydrins and dichlorohydrins of glycerol, which have been found to have combined concentrations of volatile chlorinated hydrocarbon by-products and chloroacetone less than 2000 ppm throughout any stage of the process. A "stage of the process" refers to equipment wherein the glycerin hydrochlorination process or reaction takes place, as well as purification trains and/or storage. The equipment may include for example, but would not be limited to, stirred tank reactors, plug flow reactors, batch reactors, transfer lines, pumps, distillation columns and heat exchange units. The above low levels (i.e. less than 2000 ppm) of volatile chlorinated hydrocarbon by-products and chloroacetone are maintained any where in the process prior to saponification.

The term glycerin, glycerol or glycerine and esters thereof may be used to describe the chemical, 1,2,3-trihydroxypropane and esters thereof.

As used herein, the term "multihydroxylated-aliphatic hydrocarbon" refers to a hydrocarbon which contains at least two hydroxyl groups attached to separate saturated carbon atoms. The multihydroxylated-aliphatic hydrocarbon may contain, but not to be limited thereby, from 2 to about 60 carbon atoms.

Any single carbon of a multihydroxylated-aliphatic hydrocarbon bearing the hydroxyl (OH) functional group must possess no more than one OH group, and must be sp3 hybridized. The carbon atom bearing the OH group may be primary, secondary or tertiary. The multihydroxylated-aliphatic hydrocarbon used in the present invention must contain at least two sp3 hybridized carbons each bearing an OH group. The multihydroxylated-aliphatic hydrocarbon includes any vicinal-diol (1,2-diol) or triol (1,2,3-triol) containing hydrocarbon including higher orders of contiguous or vicinal repeat units. The definition of multihydroxylated-aliphatic hydrocarbon also includes for example one or more 1,3- 1,4-, 1,5- and 1,6-diol functional groups as well. The multihydroxylated-aliphatic hydrocarbon may also be a polymer such as polyvinylalcohol. Geminal-diols, for example, would be precluded from this class of multihydroxylated-aliphatic hydrocarbon compounds.

It is to be understood that the multihydroxylated-aliphatic hydrocarbon can contain aromatic moieties or heteroatoms including for example halide, sulfur, phosphorus, nitrogen, oxygen, silicon, and boron heteroatoms; and mixtures thereof.

"Chlorohydrin" is used herein to describe a compound containing at least one hydroxyl group and at least one chlorine atom attached to separate saturated carbon atoms. A chlorohydrin that contains at least two hydroxyl groups is also a multihydroxylated-aliphatic hydrocarbon. Accordingly, the starting material and product of the present invention can each be chlorohydrins; in that case, the product chlorohydrin is more highly chlorinated than the starting chlorohydrin, i.e., has more chlorine atoms and fewer hydroxyl groups than the starting chlorohydrin. A preferred chlorohydrin is a chlorohydrin used, for example, as a starting material. A more preferred highly chlorinated chlorohydrin such as a dichlorohydrin, may be, for example, a product of the process of the present invention.

Multihydroxylated-aliphatic hydrocarbons useful in the present invention include for example 1,2-ethanediol; 1,2-propanediol; 1,3-propanediol; 1-chloro-2,3-propanediol; 2-chloro-1,3-propanediol; 1,4-butanediol; 1,5-pentanediol; cyclohexanediols; 1,2-butanediol; 1,2-cyclohexanedimethanol; 1,2,3-propanetriol (also known as, and used herein interchangeable as, "glycerin", "glycerine", or "glycerol"); and mixtures thereof. Preferably, the multihydroxylated-aliphatic hydrocarbons used in the present invention include for example 1,2-ethanediol; 1,2-propanediol; 1,3-propanediol; and 1,2,3-propanetriol; with 1,2,3-propanetriol being most preferred.

Examples of esters of multihydroxylated-aliphatic hydrocarbons useful in the present invention include for example ethylene glycol monoacetate, propanediol monoacetates, glycerin monoacetates, glycerin monostearates, glycerin diacetates, and mixtures thereof. In one embodiment, such esters can be made from mixtures of multihydroxylated-aliphatic hydrocarbons with exhaustively esterified multihydroxylated-aliphatic hydrocarbons, for example mixtures of glycerol triacetate and glycerol.

The multihydroxylated-aliphatic hydrocarbons or esters thereof of the present invention, such as glycerin or esters thereof, may be used in any desirable non-limiting concentration. In general, higher concentrations of glycerin or esters thereof are preferred for economic reasons. Useful concentrations of glycerin or esters thereof for the present invention may include, for example from about 0.01 mole % to about 99.99 mole %, preferably from about 1 mole % to about 99.5 mole %, more preferably from about 5 mole % to about 99 mole %, and most preferably from about 10 mole % to about 95 mole %. The source of glycerin may be derived from a biomass material or more preferably an oleochemical material. These glycerin feedstocks would include glycerin derived from a biodiesel process or alternatively, glycerin derived from hydrogenolysis of a cellulosic, starch or carbohydrate material. These types of feedstocks are termed "renewable" because they are not based upon hydrocarbon sources such as propylene.

The hydrogen chloride source used in the present invention is preferably introduced as a gas, a liquid or in a solution or a mixture, or a mixture thereof, such as for example a mixture of hydrogen chloride and nitrogen gas, so long as the required partial pressures of the hydrogen chloride are provided for the process of the present invention.

The most preferred hydrogen chloride source is hydrogen chloride gas. Other forms of chloride may be employed in the present invention provided that the required partial pressure of hydrogen chloride is generated. Non-volatile chloride in particular may be introduced with any number of cations including those associated with phase transfer reagents such as quaternary ammonium and phosphonium salts (for example tetra-butylphosphonium chloride). Alternatively, ionic liquids such n-butyl-2-methylimidazolium chloride may be used as a synergist to promote the acid catalyzed displacement of OH from glycerin. A cheap and convenient approach to raising the steady state concentration of reactive chloride throughout the process would be to add NaCl or KCl to the reaction medium, especially in the hydrochlorination of glycerin containing water of reaction. Not to be bound by any specific reactor design, the source of non-volatile chloride may be of a homogeneous nature where it circulates throughout a batch or continuous process and participates in the ultimate displacement of water groups from glycerin Likewise, this co-reactant can be introduced to a batch or continuous process in a heterogeneous format. For example, NaCl pellets or a polymer bound form of phase transfer chloride source could be employed in a fixed-bed or basket format. The polymer may be a crosslinked divinylbenzene/styrene copolymer to which an alkylarylammonium cation is covalently linked and ion paired with chloride anion. These types of ion exchange resins are commercially available and are derived from chloromethylated polymer beads.

The term, "non-volatile" only relates to the manner in which the chloride containing co-reactant is introduced to the reactor configuration. Non-volatile forms of chloride can undergo exchange with HCl in the process or can be slightly soluble or at least reactive in the hydrochlorination process.

It is also known that these other halide sources may act as co-catalysts for the hydrochlorination of alcohols. In this respect catalytic amounts of iodide or bromide may be used to accelerate these reactions. These reagents may be introduced as gases, liquids or as counterion salts using a phase transfer or ionic liquid format. The reagents may also be introduced as metal salts wherein the alkali or transition metal counterion does not promote oxidation of the glycerin or glycerin ester. Mixtures of different sources of halide may be employed, for example hydrogen chloride gas and an ionic chloride, such as tetraalkylammonium chloride or a metal halide. For example, the metal halide may be sodium chloride, potassium iodide, potassium bromide and the like.

A commercial process for the regioselective hydrochlorination of glycerin based upon the tenets of the previously disclosed superatmospheric hydrochlorination process without substantial water removal produces insignificant by-product impurities relative to the alternative art. Mitigation of chloroethers, chloroacetone, 2,3-dichloro-1-propene 1,3-dichloro-2-propanone and trichloropropane are also inherent advantages to our previously disclosed process.

The process for the hydrochlorination of a glycerin or glycerin ester may be of batch nature, continuous or semi-continuous in nature, with or without removal of chlorohydrin products. When the multihydroxylated aliphatic hydrocarbon is glycerin and the operation is run in a continuous or semicontinuous fashion, chlorohydrins may be removed via distillation at a point of high glycerin conversion wherein substantial water removal has not taken place. A suitable glycerin conversion range would be generally from about 50 to about 100%, preferably from about 60 to about 100%, more preferably from about 80 to about 100%, and most preferably from about 98 to about 100%. In such a case the corresponding conversion of monochlorohydrin (MCH) to dichlorohydrin (DCH) is generally from about 80 to about 90%, preferably from about 85 to about 95% and more preferably from about 90 to about 99.5%. Rectification of the DCH by overhead distillation at a stage in this process could allow for recycle of the any unconverted intermediates in the hydrochlorination process. These unconverted intermediates would include, for example, traces of glycerin, MCH residues and catalytic esters thereof as well as non-volatile chlorinated ethers.

Unexpectedly, it has been found that a low level of halogenated ketones such as chloroacetone and any other volatile chlorinated hydrocarbon by-products persists in DCH streams that are rectified via a distillation process after a batch or continuous hydrochlorination process, which utilizes a catalyst, a source of super-atmospheric hydrogen chloride and occurs without substantial water removal. There are also lower levels of volatile chlorinated hydrocarbon by-products including chloroacetone in non-distilled DCH products at high levels of glycerin conversion. Levels of volatile chlorinated hydrocarbon by-products including chloroacetone in the DCH streams without a removal step are generally less than about 2000 ppm, preferably less than about 1000 ppm, more preferably about 500 ppm, even more preferably less than about 300 ppm, most preferably less than about 100 ppm and even most preferably below about 50 ppm. Levels of volatile chlorinated hydrocarbon by-products including chloroacetone in the distilled process stream are generally less than about 2000 ppm, preferably less than about 1000 ppm, more preferably about 500 ppm, even more preferably less than about 300 ppm, most preferably less than about 100 ppm and even most preferably below about 50 ppm.

By-product halogenated hydrocarbons or volatile chlorinated hydrocarbon by-products would include, for example, 1,2,3-trichloropropane and isomers thereof, 1,3-dichloropropene, 1,2-dichloropropene, 2,3-dichloro-1-propene, 2-chloro-2-propene-1-ol, 3-chloro-propene-1-ol; isomers thereof; and/or derivatives thereof; and mixtures thereof. To be certain these are volatile components, which without careful fractionation, may contaminate distilled DCH streams. The current process reduces these levels over those produced in the prior art. For the purpose of clarity, high boiling components which contain chlorine, for example MCH intermediates and chlorinated ethers of glycerin, although produced at lower levels in the current invention, are not to be considered as volatile chlorinated hydrocarbon by-products. High boiling components such as these may be recycled or purged from the process at some point in a continuous mode of operation.

In an embodiment of the present invention where the multihydroxylated-aliphatic hydrocarbon is the starting material, as opposed to an ester of the multi-hydroxylated aliphatic hydrocarbon as a starting material, it is preferred that the formation of chlorohydrin be promoted by the presence of a catalyst. In another embodiment of the present invention, where the ester of the multihydroxylated-aliphatic hydrocarbon is used as the starting material, preferably a partial ester, the catalyst exists inherently in the ester, and therefore the use of a separate catalyst component is optional. However, an additional catalyst may still be included in the present process to further promote conversion to the desired products. Additional catalyst may also be used in the case where the starting material includes a combination of esterified and nonesterifed multihydroxylated-aliphatic hydrocarbons.

When a catalyst is used in the superatmospheric pressure process of the present invention, the catalyst may be for example a carboxylic acid; an anhydride; an acid chloride; an ester; a lactone; a lactam; an amide; a metal organic compound such as sodium acetate; or a combination thereof. Any compound that is convertible to a carboxylic acid or a functionalized carboxylic acid under the reaction conditions of the present invention may also be used.

A preferred carboxylic acid for the superatmospheric pressure process is an acid with a functional group consisting of a halogen, an amine, an alcohol, an alkylated amine, a sulfhydryl, an aryl group or an alkyl group, or combinations thereof, wherein this moiety is not sterically hindering the carboxylic acid group. A preferred acid for this present process is acetic acid.

Examples of carboxylic acids usefulness as a catalyst in the present invention include, acetic acid, propionic acid, 4-methylvaleric acid, adipic acid, 4-droxyphenylacetic acid, 6-chlorohexanoic acid, 4-aminobutyric acid, hexanoic acid, heptanoic acid, 4-dimethylaminobutyric acid, 6-aminohexanoic acid, 6-hydroxyhexanoic acid, 4-aminophenylacetic acid, 4-trimethylammonium butyric acid chloride, polyacrylic acid, polyethylene grafted with acrylic acid, a divinylbenzene/methacrylic acid copolymer, and mixtures thereof. Examples of anhydrides include acetic anhydride, maleic anhydride, and mixtures thereof. Examples of acid chlorides include acetyl chloride, 6-chlorohexanoyl chloride, 6-hydroxyhexanoyl chloride and mixtures thereof. Examples of esters include methyl acetate, methyl propionate, methyl pivalate, methyl butyrate, ethylene glycol monoacetate, ethylene glycol diacetate, propanediol monoacetates, propanediol diacetates, glycerin monoacetates, glycerin diacetates, glycerin triacetate, a glycerin ester of a carboxylic acid (including glycerin mono-, di-, and tri-esters), and combinations thereof. Examples of most preferred lactones include ε-caprolactone, γ-butyrolactone, δ-valerolactone and mixtures thereof. An example of a lactam is ε-caprolactam. Zinc acetate is an example of a metal organic compound.

A preferred catalyst used in the present invention is a carboxylic acid, an ester of a carboxylic acid, or a combination thereof, particularly an ester or acid having a boiling point higher than that of the desired highest boiling chlorohydrin that is formed in the reaction mixture so that the chlorohydrin can be removed without removing the catalyst. Catalysts which meet this definition and are useful in the present invention include for example, polyacrylic acid, glycerin esters of carboxylic acids (including glycerin mono-, di-, and tri-esters), polyethylene grafted with acrylic acid, 6-chlorohexanoic acid, 4-chlorobutanoic acid, caprolactone, heptanoic acid, 4-hydroxyphenylacetic acid, 4-aminophenylacetic acid, 6-hydroxyhexanoic acid, 4-aminobutyric acid, 4-trimethylammoniumbutyric acid chloride, stearic acid, 5-chlorovaleric acid, 6-hydroxyhexanoic acid, 4-aminophenylacetic acid, and mixtures thereof.

Carboxylic acids, RCOOH, catalyze the hydrochlorination of multihydroxylated-aliphatic hydrocarbons to chlorohydrins. The specific carboxylic acid catalyst chosen for the process of the present invention may be based upon a number of factors including for example, its efficacy as a catalyst, its cost, its stability to reaction conditions, and its physical properties. The particular process, and process scheme in which the catalyst is to be employed may also be a factor in selecting the particular catalyst for the present process. The "R" groups of the carboxylic acid may be chosen from hydrogen or hydrocarbyl groups, including alkyl, aryl, aralkyl, and alkaryl. The hydrocarbyl groups may be linear, branched or cyclic, and may be substituted or un-substituted. Permissible substituents include any functional group that does not detrimentally interfere with the performance of the catalyst, and may include heteroatoms. Non-limiting examples of permissible functional groups include chloride, bromide, iodide, hydroxyl, phenol, ether, amide, primary amine, secondary amine, tertiary amine, quaternary ammonium, sulfonate, sulfonic acid, phosphonate, and phosphonic acid.

The carboxylic acids useful in the present invention may be monobasic such as acetic acid, formic acid, propionic acid, isobutyric acid, hexanoic acid, heptanoic acid, oleic acid, or stearic acid; or polybasic such as succinic acid, adipic acid, or terephthalic acid. Examples of aralkyl carboxylic acids include phenylacetic acid and 4-aminophenylacetic acid. Examples of substituted carboxylic acids include 4-aminobutyric acid, 4-dimethylaminobutyric acid, 6-aminocaproic acid, 4-aminophenylacetic acid, 4-hydroxyphenylacetic acid, lactic acid, glycolic acid, 4-dimethylaminobutyric acid, and 4-trimethylammoniumbutyric acid. Additionally, materials that can be converted into carboxylic acids under reaction conditions, including for example carboxylic acid halides, such as acetyl chloride; carboxylic acid anhydrides such as acetic anhydride; carboxylic acid esters such as methyl acetate; multihydroxylated-aliphatic hydrocarbon acetates such as glycerol 1,2-diacetate; carboxylic acid amides such as ε-caprolactam and γ-butyrolactam; and carboxylic acid lactones such as γ-butyrolactone, δ-valerolactone and ε-caprolactone may also be employed in the present invention. Mixtures of carboxylic acids may also be used in the present invention.

Some carboxylic acid catalysts that may be used in the present invention are less effective than others in the hydrochlorination process of the present invention, such as those bearing sterically demanding substituents close to the carboxylic acid group, for example 2,2-dimethylbutyric acid, sterically hindered 2-substituted benzoic acids such as 2-aminobenzoic acid and 2-methylaminobenzoic acid. For this reason, carboxylic acids that are sterically unencumbered around the carboxylic acid group are more preferred.

In the process of the present invention utilizing superatmospheric partial pressure of HCl conditions, preferred acid catalysts used in the present invention include for example acetic acid, propionic acid, butyric acid, isobutyric acid, hexanoic acid, heptanoic acid, 4-hydroxyphenylacetic acid, 4-aminophenylacetic acid, 4-aminobutyric acid, 4-dimethylaminobutyric acid, 4-trimethylammonium butyric acid chloride, succinic acid, 6-chlorohexanoic acid, 6-hydroxyhexanoic acid, and mixtures thereof.

In another embodiment of the present invention, some of the catalysts of the present invention that work in the superatmospheric pressure process described above may also work surprisingly well at atmospheric and subatmospheric pressure conditions with or without water removal. Accordingly, one embodiment of the present invention is directed to a process for producing a chlorohydrin, an ester of a chlorohydrin, or a mixture thereof comprising the step of contacting a multihydroxylated-aliphatic hydrocarbon, an ester of a multihydroxylated-aliphatic hydrocarbon, or a mixture thereof with a source of a superatmospheric atmospheric or subatmospheric partial pressure of hydrogen chloride to produce a chlorohydrin, an ester of a chlorohydrin, or a mixture thereof, in the presence of a catalyst, wherein the catalyst (i) is a carboxylate derivative having from two to about 20 carbon atoms and containing at least one functional group selected from the group comprising an amine, an alcohol, a halogen, an sulfhydryl, an ether, an ester, or a combination thereof, wherein the functional group is attached no closer to the acid function than the alpha carbon; or a precursor thereto; (ii) is less volatile than the chlorohydrin, ester of a chlorohydrin, or a mixture thereof; and (iii) contains heteroatom substituents.

One embodiment of the catalyst structure of the present invention is generally represented by Formula (a) shown below wherein the functional group "R" includes a functional group comprising an amine, an alcohol, a halogen, a sulfhydryl, an ether; or an alkyl, an aryl or alkaryl group of from 1 to about 20 carbon atoms containing said functional group; or a combination thereof; and wherein the functional group "R" may include a hydrogen, an alkali, an alkali earth or a transition metal or a hydrocarbon functional group.

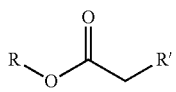

Formula (a)

In accordance with this embodiment of the present invention, certain catalysts may also be advantageously employed at superatmospheric, atmospheric or sub-atmospheric pressure, and particularly in circumstances where water is continuously or periodically removed from the reaction mixture to drive conversion to desirably higher levels. For example, the hydrochlorination of glycerol reaction can be practiced by sparging hydrogen chloride gas through a mixture of a multihydroxylated-aliphatic hydrocarbon and a catalyst. In such a process, a volatile catalyst, such as acetic acid, may be at least partially removed from the reaction solution by the hydrogen chloride gas being sparged through the solution and may be lost from the reaction medium. The conversion of the multihydroxylated-aliphatic hydrocarbon to desired chlorohydrins may consequently be slowed because the catalyst concentration is reduced. In such a process, the use of less volatile catalysts, such as 6-hydroxyhexanoic acid, 4-aminobutyric acid; dimethyl 4-aminobutyric acid; 6-chlorohexanoic acid; caprolactone; carboxylic acid amides such as ε-caprolactam and γ-butyrolactam; carboxylic acid lactones such as γ-butyrolactone, δ-valerolactone and ε-caprolactone; caprolactam; 4-hydroxyphenyl acetic acid; 6-aminocaproic acid; 4-aminophenylacetic acid; lactic acid; glycolic acid; 4-dimethylaminobutyric acid; 4-trimethylammoniumbutyric acid; and combination thereof; and the like may be preferred. It is most desirable to employ a catalyst, under these atmospheric or subatmospheric conditions, that is less volatile than the desired chlorohydrin being produced. Furthermore, it is desirable that the catalyst be fully miscible, with the multihydroxylated-aliphatic hydrocarbon employed. If the catalyst is not fully miscible, it may form a second phase and the full catalytic effect may not be realized. For this reason, it may be desirable that the catalyst contain polar heteroatom substituents such as hydroxyl, amino or substituted amino, or halide groups, which render the catalyst miscible with the multihydroxylated-aliphatic hydrocarbon, for example, glycerol.

The choice of a catalyst, for example a carboxylic acid catalyst, for use in the process of the present invention may also be governed by the specific process scheme employed for multihydroxylated-aliphatic hydrocarbon hydrochlorination. For example, in a once-through process where a multihydroxylated-aliphatic hydrocarbon is reacted to as high a conversion as possible to the desired chlorohydrin, which then is further converted to other products without separation from the catalyst, the carboxylic acid catalyst is subsequently not utilized further. In such a process scheme, it is desirable that the carboxylic acid be inexpensive, in addition to being effective. A preferred carboxylic acid catalyst in such a situation would be for example acetic acid.

In a recycle process, for example, wherein the produced chlorohydrins are separated from the carboxylic acid catalyst before further processing or use, the carboxylic acid catalyst is additionally chosen based on the ease of separation of the catalyst, and its esters with the reaction products, from the desired chlorohydrin products. In such a case, it may be preferable to employ a heavy (i.e. lower volatility) acid so that it can be readily recycled to the reactor with unreacted glycerol or intermediate monochlorohydrins for further reaction. Suitable heavy acids useful in the present invention include for example 4-hydroxyphenylacetic acid, heptanoic acid, 4-aminobutyric acid, caprolactone, 6-hydroxyhexanoic acid, 6-chlorohexanoic acid, 4-dimethylaminobutyric acid, 4-trimethylammoniumbutyric acid chloride, and mixtures thereof. A recycle process would likely be performed in a continuous or semi-continuous fashion.

It is also preferred that the acid, or its esters with the multihydroxylated-aliphatic hydrocarbon being hydrochlorinated, or its esters with the reaction intermediates or reaction products be miscible in the reaction solution. For this reason it may be desirable to select the carboxylic acid catalyst taking these solubility constraints into consideration. Thus, for example, if the multihydroxylated-aliphatic hydrocarbon being hydrochlorinated is very polar, such as glycerol, some carboxylic acid catalysts would exhibit less than complete solubility, and would form two phases upon mixing. In such a case, a more miscible acid catalyst, such as acetic acid or 4-aminobutyric acid may be desirable.

The catalysts useful in the present invention are effective over a broad range of concentrations, for example from about 0.01 mole % to about 99.9 mol % based upon the moles of multihydroxylated-aliphatic hydrocarbon, preferably from about 0.1 mole % to about 67 mole %, more preferably from about 0.5 mole % to about 50 mole % and most preferably from about 1 mole % to about 40 mole %. The specific concentration of catalyst employed in the present invention may depend upon the specific catalyst employed in the present invention and the process scheme in which such catalyst is employed.

For example, in a once-through process where the catalyst is used only once and then discarded, it is preferred to employ a low concentration of a highly active catalyst. In addition, it may be desirable to employ an inexpensive catalyst. In such a process, concentrations of for example, from about 0.01 mole % to about 10 mole % based on the multihydroxylated-aliphatic hydrocarbon may be used, preferably from about 0.1 mole % to about 6 mole %, more preferably from about 1 mole % to about 5 mole %.

In process schemes, for example, where the catalyst is recycled and used repeatedly, it may be desirable to employ higher concentrations than with a catalyst that is discarded. Such recycled catalysts may be used from about 1 mole % to about 99.9 mole % based on the multihydroxylated-aliphatic hydrocarbon, preferably from about 5 mole % to about 70 mole %, more preferably from about 5 mole % to about 50 mole %, although these concentrations are to be considered non-limiting. Higher catalysts concentrations may be desirably employed to reduce the reaction time, minimize the size of process equipment and reduce the formation of undesirable, uncatalyzed side products.

Generally, it is preferred that the process of the present invention is carried out under superatmospheric pressure conditions. "Superatmospheric pressure" herein means that the hydrogen chloride (HCl) partial pressure is above atmospheric pressure, i.e. 15 psia or greater. Generally, the hydrogen chloride partial pressure employed in the process of the present invention is at least about 15 psia HCl or greater. Preferably, the pressure of the present process is not less than about 25 psia, more preferably not less than about 35 psia HCl, and most preferably not less than about 55 psia; and preferably not greater than about 1000 psia HCl, more preferably not greater than about 600 psia, and most preferably not greater than about 150 psia.

The HCl used in the present invention is most preferably anhydrous. The HCl composition can range from 100 volume % hydrogen chloride to about 50 volume % hydrogen chloride. Preferably, the HCl feed composition is greater than about 50 volume % HCl, more preferably greater than about 90 volume % HCl, and most preferably greater than about 99 volume % HCl.

The temperatures useful in the practice of the process of the present invention are sufficient to give economical reaction rates, but not so high that starting material, product or catalyst stability become compromised. Furthermore, high temperatures increase the rate of undesirable uncatalyzed reactions, such as non-selective over-chlorination, and can result in increased rates of equipment corrosion. Useful temperatures in the present invention generally may be from about 25° C. to about 300° C., preferably from about 25° C. to about 200° C., more preferably from about 30° C. to about 160° C., even more preferably from about 40° C. to about 150° C., and most preferably from about 50° C. to about 140° C.

The reaction of the superatmospheric pressure process of the present invention is advantageously rapid and may be carried out for a time period of less than about 12 hours, preferably less than about 5 hours, more preferably less than about 3 hours and most preferably less than about 2 hours. At longer reaction times, such as above about 12 hours, the process begins to form RCls and other over-chlorinated by-products.

Surprisingly, it has been discovered that high per-pass yields and high selectivity can be achieved using the superatmospheric pressure process of the present invention. For example, a per-pass yield for the chlorohydrin based on the multihydroxylated-aliphatic hydrocarbon of greater than about 80%, preferably greater than about 85%, more preferably greater than about 90%, and most preferably greater than about 93% can be achieved by the present invention. For example, a high selectivity of greater than about 80%, preferably greater than about 85%, more preferably greater than about 90%, and most preferably greater than about 93% of chlorohydrins can be achieved by the process of the present invention. Of course, yields can be increased by recycling reaction intermediates.

For example, when the multihydroxylated-aliphatic hydrocarbon used in the present invention is glycerol, recycling intermediate monochlorohydrins can increase the ultimate yield of dichlorohydrins achieved. Moreover, unlike many of the processes of the prior art, water removal is not an essential feature of the process of the present invention in carrying out the reaction which forms the chlorohydrins. In fact, the reaction of the present invention is preferentially carried out in the absence of water removal such as azeotropic removal of water.

In the superatmospheric pressure process of the present invention, it is also not necessary to use starting materials that are free of contaminants such as water, salts or organic impurities other than multihydroxylated-aliphatic hydrocarbons. Accordingly, the starting materials may contain, generally, no more than about 50 weight percent of such contaminants. For example, crude 1,2,3-propanetriol (crude glycerol) that may contain water (from about 5% to about 25% weight percent), alkali (for example, sodium or potassium) or alkaline earth (for example, calcium or magnesium) metal salts (from about 1% to about 20% by weight), and/or alkali carboxylate salts (from about 1% to about 5% by weight), can also be used in the present invention effectively to produce the desired product. Consequently, the process of the present invention is a particularly economical approach.

In one embodiment of the process of the present invention, 1,2,3-propanetriol (glycerol) is placed in a closed vessel, and heated and pressurized under an atmosphere of HCl gas in the presence of the aforementioned catalytic amount of a carboxylic acid or ester thereof. Under the preferred conditions of the process, the major product is 1,3-dichloropropan-2-ol (for example, >90% yield), with minor amounts (for example, <10% total yield) of the following products: 1-chloro-2,3-propanediol, 2-chloro-1,3-propanediol and 2,3-dichloropropan-1-ol; and no detectable amounts (less than 200 ppm) of 1,2,3-trichloropropane. Advantageously, both the major and minor dichlorinated products (1,3-dichloro-propan-2-ol and 2,3-dichloropropan-1-ol) are precursors to epichlorohydrin. The dichlorinated products can readily be converted to epichlorohydrin by reaction with base, as is well-known in the art.

The present invention may include various process schemes, including for example batch, semi-batch, or continuous. In one embodiment, for example, the present invention includes the hydrochlorination of a multihydroxylated-aliphatic hydrocarbon by reaction with hydrogen chloride. The multihydroxylated-aliphatic hydrocarbon may be employed neat or diluted in an appropriate solvent. Such solvents may include for example water and alcohols. It may be preferred to purify the multihydroxylated-aliphatic hydrocarbon before it is employed in the hydrochlorination reaction by removing contaminants, including water, organic materials or inorganic materials before use. This purification may include well known purification techniques such as distillation, extraction, absorption, centrifugation, or other appropriate methods. The multihydroxylated-aliphatic hydrocarbon is generally fed to the process as a liquid although this is not absolutely necessary.

The hydrogen chloride employed in the process is preferably gaseous. The hydrogen chloride may, however, be diluted in a solvent such as an alcohol (for example methanol); or in a carrier gas such as nitrogen, if desired. Optionally, the hydrogen chloride may be purified before use to remove any undesirable contaminants. It is preferred that the hydrogen chloride be substantially anhydrous although some amounts (for example less than about 50 mole %, preferably less than about 20 mole %, more preferably less than about 10 mole %, even more preferably less than about 5 mole %, most preferably less than about 3 mole %) of water present in the hydrogen chloride are not excessively detrimental. The hydrogen chloride is fed to the process equipment in any suitable manner. It is preferred that the process equipment is designed to ensure good dispersal of the hydrogen chloride throughout the hydrochlorination reactor that is employed in the present process. Therefore, single or multiple spargers, baffles and efficient stirring mechanisms are desirable.

The catalyst employed may be fed to the process equipment independently, or as a mixture with, or component of, the multihydroxylated-aliphatic hydrocarbon or hydrogen chloride feeds.

The equipment useful for the hydrochlorination reaction of the present invention may be any well-known equipment in the art and should be capable of containing the reaction mixture at the conditions of the hydrochlorination. Suitable equipment may be fabricated of materials which are resistant to corrosion by the process components, and may include for example, metals, such as tantalum, suitable metallic alloys such as Hastalloy C©, or glass-lined equipment. Suitable equipment may include, for example, single or multiple stirred tanks, tubes or pipes, or combinations thereof.

In an exemplifying batch process, the multihydroxylated aliphatic hydrocarbon and hydrochlorination catalyst are charged to a reactor. Hydrogen chloride is then added to the desired pressure and the reactor contents heated to the desired temperature for the desired length of time. The reactor contents are then discharged from the reactor and either purified or sent to other equipment for further processing, or to storage.

In an illustrative semi-batch process, one or more of the reagents is fed to a reactor over a period of time throughout the reaction while other reagents are fed only at the start of the reaction. In such a process, for example, the multihydroxylated-aliphatic hydrocarbon and catalyst may be fed in a single batch to a hydrochlorination reactor, which is then held at reaction conditions for a suitable time, while hydrogen chloride is fed continuously throughout the reaction at the desired rate, which may be at constant flow, or constant pressure. After the reaction, the hydrogen chloride feed can be terminated and the reactor contents may be discharged for storage, purification or further processing.

In the large-scale production of chemicals it is often desirable to employ a continuous process since the economic advantage of doing so is usually greater than for batch processing. The continuous process may be, for example, a single-pass or a recycle process. In a single-pass process, one or more of the reagents pass through the process equipment once, and then the resulting effluent from the reactor is sent for purification or further processing. In such a scheme, the multihydroxylated-aliphatic hydrocarbon and catalyst may be fed to the equipment and hydrogen chloride added as desired at a single point or at multiple points throughout the process equipment, which may include continuous stirred tank reactors, tubes, pipes or combinations thereof.

Alternatively, the catalyst employed may be a solid which is retained within the process equipment by means of a filter or equivalent device. The reagents and catalysts are fed at such a rate that the residence time in the process equipment is appropriate to achieve a desired conversion of the multihydroxylated-aliphatic hydrocarbon to products. The material exiting the process equipment is sent to storage, for purification or further processing, as desired. In such a process, it is generally desirable to convert as much multihydroxylated-aliphatic hydrocarbon to desired product as possible.

In a continuous recycle process, one or more of the unreacted multihydroxylated-aliphatic hydrocarbon, reaction intermediates, hydrogen chloride, or catalyst exiting from the process equipment are recycled back to a point earlier in the process. In this manner, raw material efficiencies are maximized or catalysts reused. Since catalysts are reused in such a process scheme, it may be desirable to employ the catalysts in a higher concentration than they are employed in a single-pass process where they are often discarded. This may result in faster reactions, or smaller process equipment, which results in lower capital costs for the equipment employed.

Removal of the desired product from the catalysts or other process components can be achieved in a variety of ways. It may be possible to achieve the separation, for example, by vaporization in a continuous fashion, either directly from the hydrochlorination reactor, or a separate piece of equipment such as a vaporizer or a distillation column. In such a case, a catalyst that is less volatile than the desired product would be employed, so that the catalyst is retained within the process equipment. Alternatively, a solid catalyst may be employed, and the separation may be achieved, for example, by filtration, centrifugation or vaporization. Liquid extraction, absorption or chemical reaction may also be employed in some cases to recycle catalysts or reaction intermediates.

In one embodiment of the present invention, a multihydroxylated-aliphatic hydrocarbon is hydrochlorinated using a hydrochlorination catalyst chosen to be less volatile than the desired hydrochlorination products. After the hydrochlorination reaction, additional multihydroxylated-aliphatic hydrocarbon is added to the reaction products, excess starting materials, reaction intermediates and catalyst. It is thought that this liberates some of the desired hydrochlorination product which may have existed as an ester of the catalyst, so that the desired product can be more completely recovered from the reaction solution by vaporization. After recovery of the desired hydrochlorination product, the remainder of the process stream can be recycled to the hydrochlorination stream. This process scheme also may have the advantage of minimizing the amount of hydrogen chloride lost since much of that remaining in the process stream after addition of multihydroxylated-aliphatic hydrocarbon would be consumed by reaction with the newly added multihydroxylated-aliphatic hydrocarbon.

The particular process scheme employed may depend upon many factors including, for example, the identity, cost and purity of the multihydroxylated-aliphatic hydrocarbon being hydochlorinated, the specific process conditions employed, the separations required to purify the product, and other factors. The examples of processes described herein are not to be considered as limiting the present invention.

Figure 2:
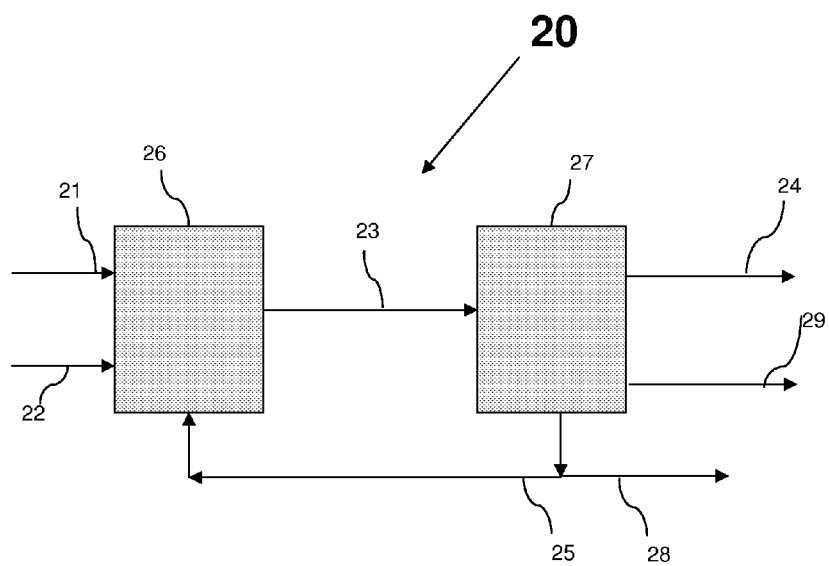
FIG. 2 is a process flowchart illustrating another embodiment of the process of the present invention referred to herein as a catalyst and intermediate recycle process.
Figure 3:
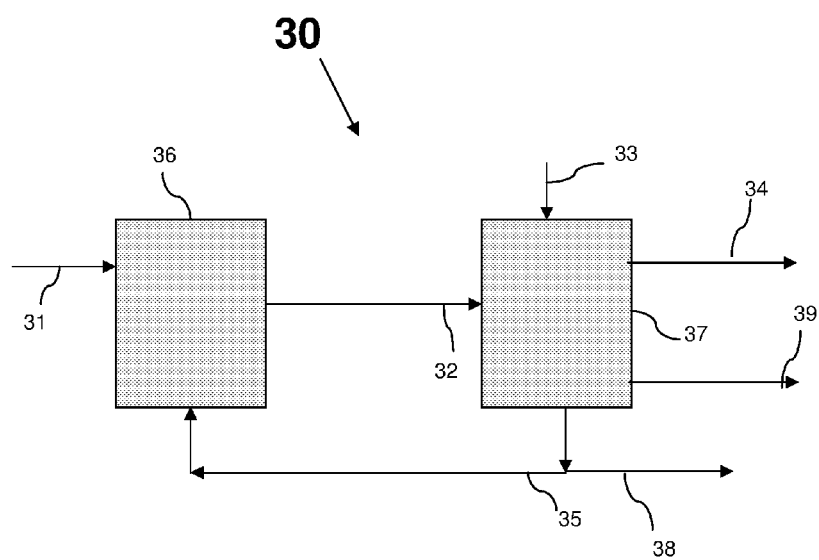
FIG. 3 is a process flowchart illustrating another embodiment of the process of the present invention referred to herein as a catalyst and intermediate recycle process with transesterification.

FIGS. 1, 2 and 3 show three non-limiting embodiments of the hydrochlorinated process of the present invention. The examples illustrating the present invention process shown in FIGS. 1, 2 and 3 are only preferred embodiments of the present invention.

FIG. 1, for example, shows a process of the present invention generally indicated by numeral 10, wherein a multihydroxylated-aliphatic hydrocarbon such as a glycerol feed stream, 11, is introduced into a reaction vessel, 15. The reaction vessel 15, may be of any well-known suitable type, including for example, one or more continuous stirred tank reactors (CSTRs) or tubular reactors; or combinations thereof.

Also introduced to vessel 15, are a hydrogen chloride feed stream, 12, and a carboxylic acid or carboxylic acid precursor catalyst feed stream, 13. Streams 12 and 13 may be introduced into vessel 15 either separately or together. In addition, optionally, all of the streams 11, 12, and 13 may be combined together into one feed stream. Any of the streams 11, 12, or 13, may be introduced at a single point or at multiple points of vessel 15. In vessel 15, glycerol is partially or fully converted to its esters with the carboxylic acid catalyst, monochlorohydrins and dichlorohydrins and their esters. Stream 14, containing, for example dichlorohydrins, monochlorohydrins, unreacted glycerol, and their esters, water, unreacted hydrogen chloride and catalyst exits vessel 15, and may be sent to storage, to further processing such as purification, or to other equipment for further reaction.

For example, in one embodiment, stream 14, may be reacted with a base to form epichlorohydrin. The carboxylic acid catalyst in such a process may be chosen based on its efficacy at low concentration and its low cost. For example, the carboxylic acid may be acetic acid or propionic acid.

FIG. 2 shows another embodiment of the process of the present invention generally indicated by numeral 20, in which a feed stream 21 containing a multihydroxylated-aliphatic hydrocarbon such as a glycerol is fed to vessel 26, which may be one or more CSTRs or tubular reactors, or combinations thereof. Also fed to vessel 26 is feed stream 22, containing hydrogen chloride. Also fed to vessel 26 is a recycle stream 25, recycled from vessel 27, containing, for example, unreacted glycerol, monochlorohydrins and their esters with the catalyst, which is also recycled in this stream 25.

In vessel 26, glycerol is converted to monochlorohydrins and their esters; and monochlorohydrins are converted to dichlorohydrins and their esters. Stream 23, containing, for example, dichlorohydrins, monochlorohydrins, unreacted glycerol and their esters with the carboxylic acid catalyst, water, unreacted hydrogen chloride and catalyst exits vessel 26, and is fed to vessel 27. In vessel 27, at least some of the desired dichlorohydrins, water, and unreacted hydrogen chloride, as stream 24, are separated from monochlorohydrins and their esters, unreacted glycerol and its esters and catalyst, as recycle stream 25, which is recycled to vessel 26. Stream 25 may also optionally contain some dichlorohydrins and their esters. Optionally, a purge stream may also exit vessel 27 as a purge stream 28 from the recycle stream 25 and/or from the vessel 27 via purge stream 29. The purge stream may comprise compositions of the recycle stream; or salts or heavies that are either fed in with the crude multihydroxylated-aliphatic hydrocarbons or produced in the process.

Vessel 27 may comprise any well-known suitable separation vessel, including one or more distillation columns, flash vessels, extraction, absorption columns, centrifuges, crystallizers, membrane separators, cyclones, evaporators, heat exchangers or filters; or any suitable known separation apparatuses known in the art. Product stream 24 may be sent to storage, to further processing for example purification, or to a further reaction, for example, conversion to epichlorohydrin. In one example of this process scheme, the catalyst may be chosen such that its chemical or physical properties result in a ready separation of the catalyst or its esters from the desired dichlorohydrins. For example, the catalyst selected for this process scheme may be 6-chlorohexanoic acid, caprolactone, 4-chlorobutyric acid, stearic acid, or 4-hydroxyphenylacetic acid.

FIG. 3 shows another embodiment of the process of the present invention generally indicated by numeral 30, in which a vessel 36 is fed with a feed stream 31, containing hydrogen chloride; and a recycle stream containing glycerol, glycerol esters, monochlorohydrin and their esters and catalyst, via stream 35. In vessel 36, which may comprise one or more CSTRs, one or more tubular reactors or combinations thereof, glycerol and monochlorohydrins are converted to dichlorohydins. Stream 32, containing, for example, dichlorohydrins, monochlorohydrins, glycerol and their esters, catalyst, unreacted hydrogen chloride and water exists vessel 36 and is fed to vessel 37. Also fed to vessel 37 is feed stream 33, containing glycerol.

In vessel 37, glycerol reacts with the esters of monochlorohydrins and dichlorohydrins to substantially liberate the free monochlorohydrins and dichlorohydrins and forming glycerol esters. Additionally, at least some of the unreacted hydrogen chloride that enters vessel 37 via stream 32 is also consumed to form mainly monochlorohydrins. Vessel 37 may also serve as a means to separate the desired dichlorohydrins from unreacted monochlorohydrins and glycerol and their esters. Vessel 37 may include, for example, one or more centrifuges, crystallizers, membrane separators, cyclones, evaporators, heat exchangers, filters, distillation columns, flash vessels, extractors, or any other separation equipment; or vessel 37 may be, for example, a combination of a stirred tank, tubular reactor or similar vessel with the aforementioned separation equipment. Product stream 34, exiting vessel 37 and containing dichlorohydrins, water and residual hydrogen chloride may be sent to storage, to further processing such as purification, or to a process for further reaction, for example to a reaction process for preparing epichlorohydrin. Stream 35, containing glycerol and monochlorohydrins and their esters and catalyst exits vessel 37 to be recycled, as stream 35, to the vessel 36. Optionally, a purge stream may also exit vessel 37 as a purge stream 38 from the recycle stream 35 and/or from the vessel 37 via purge stream 39. The purge stream may comprise compositions of the recycle stream; or salts or heavies that are either fed in with the crude multihydroxylated-aliphatic hydrocarbons or produced in the process.

Some or all of the equipment described above with reference to FIGS. 1, 2 and 3 may be made of corrosion resistant materials which are well known in the art.

In the process configuration of FIG. 3, it may be desirable to use relatively large amounts of catalyst, for example from about 10 mole % to about 70 mole % based on glycerol so that the rate of the hydrochlorination reaction in vessel 36 is very fast, and the equipment consequently small. It is also preferred that the catalyst, in the process configuration of FIG. 3, possess chemical or physical properties such that the separation in vessel 37 is facilitated, for example, the use of a catalyst that boils at a temperature substantially below that at which the lowest boiling dichlorohydrins boils may be preferred when the separation method is distillation. Examples of such catalysts include 6-chlorohexanoic acid, heptanoic acid, and 4-hydroxyphenylacetic acid.

The present invention also includes a novel composition made by the process of the present invention. The compositions of the present invention made by the present process includes for example, dichlorohydrins made from glycerol. Such dichlorohydrins made by the present process are useful in that they comprise high concentration of dichlorohydins, (i.e. 1,3-dichloropropan-2-ol and 2,3-dichloropropan-1-ol) high ratios of the two isomers of dichlorohydrins and their esters, i.e. high ratios of 1,3-dichloropropan-2-ol and esters to 2,3-dichloropropan-1-ol and esters, low concentrations of glycerol and its esters and monochlorohydrins, i.e. 2-chloro-1,3-propanediol and 1-chloro-2,3-propanediol and their esters, and low concentrations of undesirable byproducts, i.e. 1,2,3-trichloropropane and chlorinated glycerol oligomeric ethers, such as bis (3-chloro-2-hydroxypropyl)ether, and their esters.

The compositions of the present invention are useful in the manufacture of epichlorohydrin, giving high yields of high purity epichlorohydrin in short reaction times with low levels of chlorinated by-products that are difficult or expensive to dispose of.

As one embodiment and an illustration of the present invention, but not to be bound thereby, useful compositions (excluding water and inorganic impurities) which may be made in accordance with the present invention, may be made for example from glycerol hydrochlorination. The following abbreviations are used in the tables below: "1,3-Dichlorohydrin" is 1,3-dichloropropan-2-ol; "2,3-dichlorohydrin" is 2,3-dichloropropan-1-ol; "Monochlorohydrins" include: 1-chloro-2,3-propanediol and 2-chloro-1,3-propanediol and mixtures thereof. Generally, such compositions include for example the following components, excluding fatty acid methyl esters and the like:

| Component | Mole % |
| --- | --- |
| Glycerol and its esters | from 0.1 to 1 |
| Monochlorohydrins and their esters | from 4 to 10 |
| 1,3-Dichlorohydrin and its esters | greater than 80 |
| 2,3-Dichlorohydrin and its esters | from 1 to 4 |
| 1,2,3-Trichloropropane | less than 0.2 |
| Chlorinated glycerol ethers and their esters | less than 0.3 |

The 1,3-dichlorohydrin to 2,3-dichlorohydrin ratio in the above composition is generally from about 8:1 to about 100:1.

Preferably, the composition of the present invention may be as follows:

| Component | Mole % |
|---|---|
| Glycerol and its esters | from 0.01 to 0.1 |
| Monochlorohydrins and their esters | from 3 to 8 |
| 1,3-Dichlorohydrin and its esters | greater than 85 |
| 2,3-Dichlorohydrin and its esters | from 1 to 3 |
| 1,2,3-Trichloropropane | less than 0.1 |
| Chlorinated glycerol ethers and their esters | less than 0.2 |

More preferably, the composition of the present invention may be as follows:

| Component | Mole % |
|---|---|
| Glycerol and its esters | from 0.001 to 0.1 |
| Monochlorohydrins and their esters | from 2 to 7 |
| 1,3-Dichlorohydrin and its esters | greater than 87 |
| 2,3-Dichlorohydrin and its esters | from 1 to 2 |
| 1,2,3-Trichloropropane | less than 0.05 |
| Chlorinated glycerol ethers and their esters | less than 0.15 |

Most preferably, the composition of the present invention may be as follows:

| Component | Mole % |
|---|---|
| Glycerol and its esters | less than 0.1 |
| Monochlorohydrins and their esters | from 1 to 5 |
| 1,3-Dichlorohydrin and its esters | greater than 90 |
| 2,3-Dichlorohydrin and its esters | from 0.1 to 2 |
| 1,2,3-Trichloropropane | less than 0.02 |
| Chlorinated glycerol ethers and their esters | less than 0.1 |

The above compositions of the present invention are useful in the manufacture of epichlorohydrin. High selectivity to 1,3-dichlorohydrin and its esters relative to the selectivity to 2,3-dichlorohydrin and its esters results in more efficient and faster formation of epichlorohydrin upon reaction with caustic. In addition, low levels of trichloropropane (TCP) in the present composition are desired because it minimizes the cost of handling and disposing of TCP. Low levels of glycerol and monochlorohydrins are also desired in the present composition to maximize glycerol raw material efficiency through high conversions to the desired dichlorohydrins.

The following examples are for illustrative purposes only and are not intended to limit the scope of the present invention.

EXAMPLE 1

Preparation of a Chlorohydrin from Glycerol

To a 100 mL Hastelloy C™ Parr reactor equipped with a Magnedrive stirrer, internal cooling coils, and a thermocouple were added glycerol (30.0 g, obtained from Sigma-Aldrich Chemical Corporation) and glacial acetic acid (4.5 g, obtained from JT Baker Corporation). The reactor was sealed, pressurized to 90 psig with anhydrous hydrogen chloride gas (Airgas Corporation), and heated to 93° C. for 90 minutes and maintained at 90 psig with anhydrous hydrogen chloride gas, after which the reactor was cooled and vented at room temperature (about 25° C.). The reactor contents (65.9 g) were collected, analyzed by gas chromatography (GC), and found to contain the following products: 1,3-dichloropropan-2-ol and its acetate ester (total 92.6 mole %) and 2,3-dichloropropan-1-ol and its acetate ester (total 1.7 mole %). Additionally, a number of monochlorinated compounds (total 4.4 mole %) were detected as well as unreacted glycerol and its esters (total 1.0 mole %). No trichloropropane was detected (with a detection limit of 200 ppm).

EXAMPLE 2

Preparation of a Chlorohydrin from Glycerol/Glycerol Ester Mixture

To a 200 mL Hastelloy C™ high pressure reactor was added a 10 mL glass volumetric flask containing dry glycerol (Aldrich pre-dried over mol sieves, 91 mg, 0.99 mmol), and triacetin (Aldrich, the tri-acetate ester of glycerol, 457 mg, 2.10 mmole). The reactor was sealed and pressurized with nitrogen to 40 psig (three pressure cycles) and was brought to 110° C. with stirring after nitrogen venting. Anhydrous HCl was introduced at a constant pressure of 76 psig and the reaction was allowed to proceed for 3 hours. The reactor was vented providing a product that was found to contain 25.90 area percent 1,3-dichloropropan-2-ol, 68.34 area percent 1,3-dichloro-2-acetoxypropane, 1.57 area percent 1,2-dichloro-3-acetoxypropane, 2.86 area percent 2-chloropropane-1,3-diacetoxypropane and no detectable glycerol, triacetin or 1,2,3-trichloropropane as determined by GC flame ionization detection analysis.

EXAMPLE 3

Preparation of a Chlorohydrin from Crude Glycerol

To a 100 mL Hastelloy™ C Parr reactor equipped with a Magnedrive stirrer, internal cooling coils, and a thermocouple, were added crude glycerol (30.0 g, obtained from Interwest Corporation) and glacial acetic acid (0.6 g, obtained from JT Baker Corporation). The reactor was sealed, pressurized to 120 psig with anhydrous hydrogen chloride gas (Airgas Corporation), and heated to 120° C. for 90 minutes while maintaining the pressure at 120 psig with the anhydrous hydrogen chloride gas. After this time, the reactor was cooled and vented at room temperature. The reactor contents (57.2 g) were collected as a mobile liquid containing a suspended white solid.

The procedure as described above was repeated and 58.0 g of reactor contents were collected from a second reaction. The two reaction products (57.2 g and 58.0 g) were then combined.

After filtration to remove the white solids, sodium and potassium salts introduced with the crude glycerol, the filtrate was analyzed by gas chromatography and found to contain 1,3-dichloropropan-2-ol (95.3 wt %), 2,3-dichloropropan-1-ol (2.6 wt %), 2-acetoxy-1,3-dichloropropane (0.7 wt %), and 1-acetoxy-2,3-dichloropropane (0.1 wt %). Additionally, a number of acetoxychloropropanols (0.87 wt %) were detected. No unreacted glycerol nor its esters, nor trichloropropanol were detected.

EXAMPLES 4-41

The following examples were performed in a 100 mL, Hastalloy C™ Parr autoclave equipped with a Magnedrive stirrer, a thermocouple and internal cooling coils. Glycerol (30 g, 326 mmol, Aldrich 99%), was added to the reactor, along with a catalyst (10 mmols) or other additives as described in Table I below, and water (3.0 g, 167 mmols), and then the reactor was sealed. The mass of the reactor and contents were recorded. The reactor was stirred and ice-cooled water was cycled through the cooling coils. Hydrogen chloride gas (Airgas Corporation) at the desired pressure of 110 psig was admitted to the reactor, typically resulting in a 15-25° C. exotherm. The reactor was heated to the desired temperature of 110° C., and the reaction allowed to proceed for four hours, while hydrogen chloride gas was fed continuously at the set pressure as the hydrogen chloride gas was consumed by reaction. The mass of hydrogen chloride fed to the reactor was measured by recoding the mass of the cylinder throughout the reaction.

After the desired reaction time of four hours had elapsed, the hydrogen chloride feed was ceased, and the reactor and contents cooled to room temperature. The reactor was then vented and the mass of the reactor and contents were recorded. The reaction product was analyzed by gas chromatography. Selectivities to dichlorohydrins are reported as 100%×moles of dichlorohydrins/moles of glycerol charged.

The following abbreviations are used herein: "1,3-DCH" is 1,3-dichloropropan-2-ol; "2,3-DCH" is 2,3-dichloropropan-1-ol; "1-MCH" is 1-chloro-2,3-propanediol; "2-MCH" is 2-chloro-1,3-propanediol; "BZIM Br" is n-butylmethylimidazolium bromide; "BZIM Cl" is n-butylmethylimidazolium chloride; "Bu4NCl.H2O" is tetra-n-butylammonium chloride hydrate; and "C16Me3NCl" is n-hexadecyltrimethylammonium chloride.

TABLE I

| | | Molar Selectivities (%) | | | |
|---|---|---|---|---|---|
| Example | Catalyst | 1,3-DCH | 2,3-DCH | 1-MCH | sum |
| 4 | Acetic acid | 90.55 | 1.93 | 1.83 | 94.31 |
| 5 | Hexanoic acid | 90.67 | 1.91 | 0.79 | 93.36 |
| 6 | 2,2-Dimethylbutyric acid | 4.63 | 0.31 | 38.39 | 43.33 |
| 7 | 3-Methylvaleric acid | 59.49 | 1.44 | 27.31 | 88.24 |
| 8 | Heptanoic acid | 87.45 | 1.82 | 3.78 | 93.04 |
| 9 | 3,3-Dimethylbutyric acid | 27.33 | 0.89 | 46.55 | 74.78 |
| 10 | 4-Trimethylammoniumbutyric acid | 79.45 | 1.81 | 13.22 | 94.48 |
| 11 | 4-Dimethylaminobutyric acid | 81.92 | 1.86 | 10.55 | 94.33 |
| 12 | 4-Aminobutyric acid | 88.60 | 1.93 | 4.13 | 94.66 |
| 13 | Glycine | 28.74 | 0.79 | 66.71 | 96.24 |
| 14 | NNN-Trimethylglycine | 5.19 | 0.26 | 43.87 | 49.32 |
| 15 | NN-Dimethylglycine | 5.37 | 0.24 | 46.95 | 52.56 |
| 16 | Glycolic Acid | 30.14 | 0.87 | 60.74 | 91.75 |
| 17 | Lactic Acid | 53.79 | 1.26 | 36.33 | 91.38 |
| 18 | 4-Dimethylaminophenylacetic acid | 72.84 | 1.61 | 16.02 | 90.47 |
| 19 | 4-Aminophenylacetic acid | 80.14 | 1.74 | 10.30 | 92.19 |
| 20 | 2-Aminobenzoic acid | 5.24 | 0.29 | 35.30 | 40.83 |
| 21 | 2-Methylaminobenzoic acid | 3.99 | 0.24 | 30.53 | 34.75 |
| 22 | 4-Hydroxyphenylacetic acid | 92.24 | 2.01 | 0.68 | 94.94 |
| 23 | Caprolactam | 67.77 | 1.39 | 17.73 | 86.89 |
| 24 | *Blank, No catalyst | 3.38 | 0.17 | 31.43 | 34.98 |
| 25 | 4-Methylvaleric acid | 88.32 | 1.97 | 0.54 | 90.83 |
| 26 | 4-Aminobenzoic acid | 31.44 | 0.92 | 30.62 | 62.98 |
| 27 | 4-Hydroxybenzoic acid | 36.85 | 1.97 | 25.27 | 64.09 |
| 28 | 4-Dimethylaminobenzoic acid | 31.07 | 0.90 | 35.18 | 67.15 |
| 29 | Heptanoic acid + 10 mmol BMIMBr | 86.98 | 1.79 | 0.98 | 89.75 |
| 30 | Heptanoic acid + 10 mmol BMIMCl | 89.95 | 1.85 | 1.07 | 92.86 |
| 31 | Heptanoic acid + 50 mmol BMIM Cl | 89.59 | 1.81 | 0.91 | 92.32 |
| 32 | Heptanoic acid + 50 mmol BMIM Br | 83.47 | 1.63 | 0.55 | 85.65 |
| 33 | Heptanoic acid + 10 mmol Bu4NCl•H2O | 87.69 | 1.76 | 0.75 | 90.20 |
| 34 | Heptanoic acid + 10 mmol C16Me3NCl | 89.84 | 1.83 | 1.23 | 92.90 |
| 35 | Phenylacetic acid | 83.96 | 1.78 | 3.36 | 89.09 |
| 36 | epsilon-Caprolactone | 93.69 | 1.93 | 0.56 | 96.17 |
| 37 | Amberlite[1] IRC-50 | 14.59 | 0.46 | 66.16 | 81.22 |
| 38 | Amberlite[1] IRP-64 | 10.93 | 0.39 | 61.07 | 72.39 |
| 39 | 6-Chlorohexanoic acid | 86.09 | 1.81 | 0.21 | 88.10 |
| 40 | beta-Butyrolactone | 64.69 | 1.55 | 17.77 | 84.02 |
| 41 | gamma-Butyrolactone | 93.69 | 1.93 | 0.56 | 96.17 |

*Example without catalyst
[1]Amberlite ® is a registered trademark of Rohm and Haas Corporation. Amberlite IRC-50 and IRP-64 are weakly acidic ion exchange resins.

COMPARATIVE EXAMPLE A

Glycerol Reaction to Dichlorohydrin with HCl, Acetic Acid and Toluene as Azeotroping Agent at Subatmospheric Pressure To a 500 mL Wharton baffled 3-necked flask equipped with overhead air stirrer, HCl inlet frit, Dean Stark trap with condenser were added glycerol (92.0 g, 1.00 mol), 5 mL of acetic acid (HOAc) and 200 mL of toluene. The reaction under positive nitrogen flow, was heated to reflux with slow purging (no rate determined or flow control) of anhydrous HCl. After 5 hours of reflux, some 23 mL of 6N aqueous HCl was collected and NMR analysis showed the resultant bottom phase to be >85% monochlorohydrin. After 3 hours another 5 mL HOAc was added and again at 6 hours; each time water evolution was very rapid after addition (1-2 mL/15 minutes in trap). The phases were miscible hot after 6 hours and then separated to two phases on cooling. The resulting products were identified by NMR versus standards and a retainer stripped of most toluene was used to provide a 122 g sample of material. The sample was analyzed using gas chromatography/mass spectrometry (GC/MS) analysis.

The results of analysis and the chemical scheme is shown in Scheme 2 below.

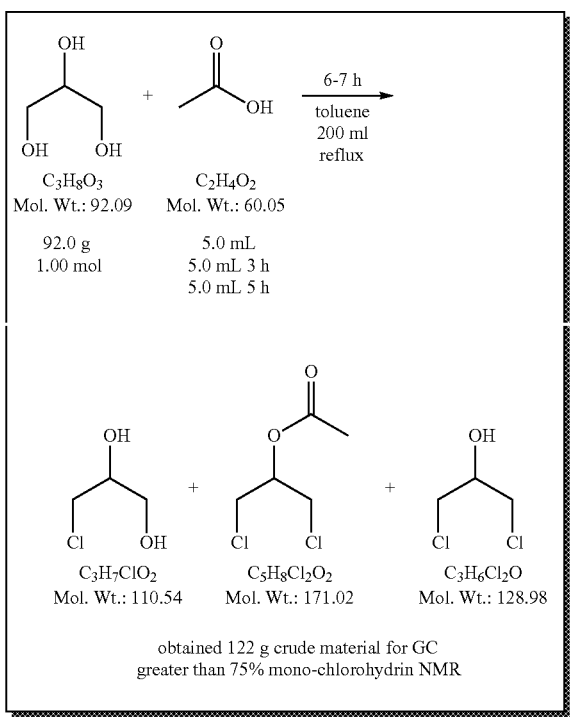

COMPARATIVE EXAMPLE B

Glycerol Reaction to Dichlorohydrin with Excess HCl Purge, Acetic Acid with No Azeotropic Water Removal and Atmospheric Pressure In this comparative example no attempt was made to rigorously remove water. To a 500 mL Wharton 3-necked flask equipped with overhead air stirrer, HCl inlet frit, and outlet to scrubber, was added 4 A sieve dried glycerol (138.0 g, 1.50 mol), 3.8 g of HOAc (2.75% based on glycerin). This outlet tube was comprised of a non-chilled 16 inch straight condenser (glass) connected to a 1/16 inch polyethylene outlet tube (approximately 7 feet) that was flanged to a 3-foot water scrubbing tower filled with burled, ceramic saddles. The reaction under positive nitrogen flow, was heated to 100° C. and then slow purging (approximately 200 mg/minute) with anhydrous HCl was commenced. The rate and total amount of added HCl was as monitored by a weigh cell. Small aliquots (for example 300 mg) of samples were taken through the side arm at appropriate intervals to complete a crude kinetic conversion profile from which half-life could be obtained. The reaction internal reaction temperature was held isothermal (100° C.±2° C.) with an temperature controller. Over a 24 hour period, a total of 700 g of anhydrous HCl was passed through the solution. The samples were analyzed using wt % GC assays and the final sample was also analyzed for water and HCl content potentiometrically to obtain a total mass balance. The resulting dark brown reaction product (minus the 200 mg retainers) after 23.75 hours of purging was 218.5 g.

Figure 4:
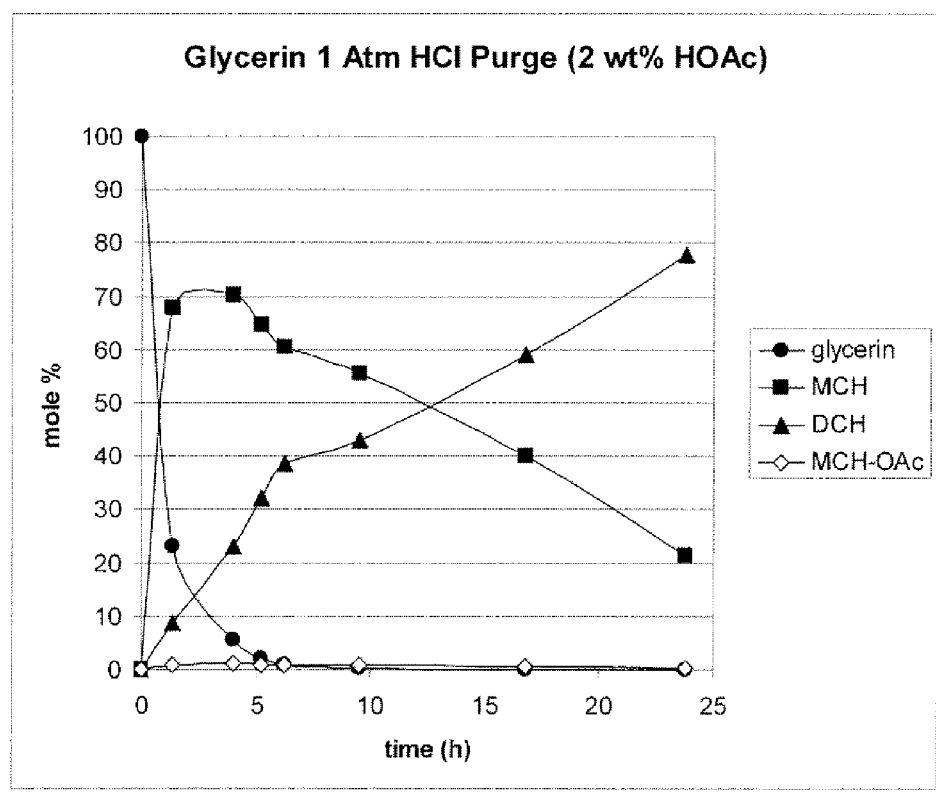
FIG. 4 is graphical illustration showing the results of the amount, in mole %, of conversion of glycerol to monochlorohydrins and dichlorohydrins as a function of time, carried out using an example that is not part of the present invention.

The results of analysis and the chemical scheme are shown in Scheme 3 below. The conversion of glycerol to monochlorohydrins and dichlorohydrins is shown graphically in FIG. 4. In FIG. 4, "MCH" is the total mole % of monochlorohydrins: 3-chloro-2,3-propanediol and 2-chloro-1,3-propanediol; "MCH-OAc" is the total mole % of acetate esters of MCH; and "DCH" is the total mole % of dichlorohydrins: 1,3-dichloropropan-2-ol and 2,3-dichloropropan-1-ol.

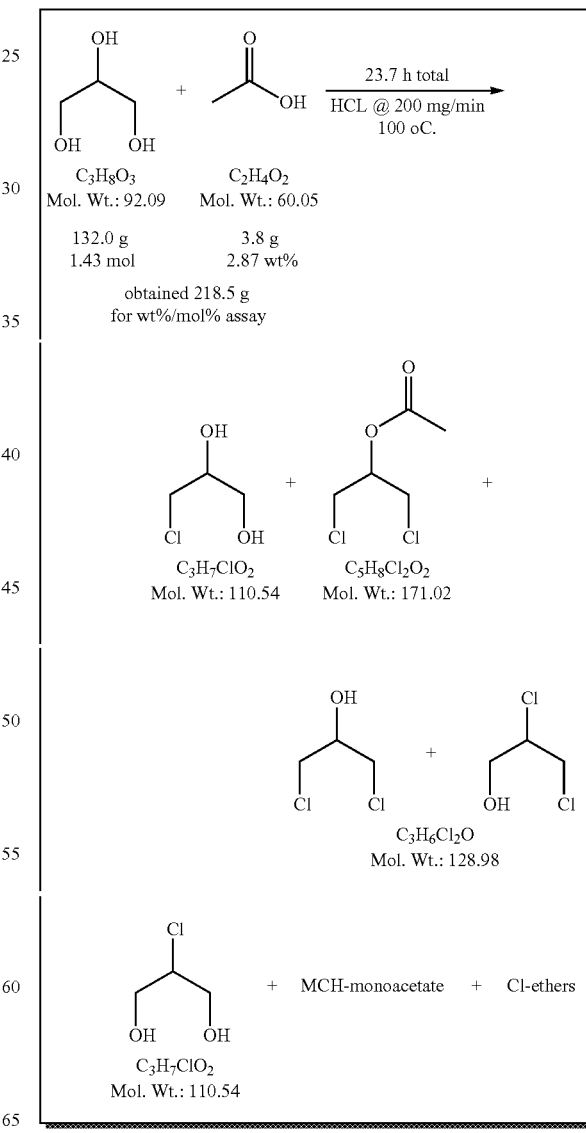

EXAMPLE 42

Glycerol Reaction to Dichlorohydrin with Pressure HCl, Acetic Acid and No Azeotropic Water Removal After nitrogen purging (two 40 psig pressure/vent cycles), dry glycerin (30.0 g, 0.320 mole) containing 4 wt % acetic acid (1.2 g Aldrich) as a catalyst was subjected to static pressures 90-96 psig of anhydrous HCl with stirring and heating in a magnetically driven, 100 mL Hasteloy-C Parr reactor. This reactor was equipped with an internal thermocouple which measured the internal solution temperature. External heating to the reactor was provided by an immersion bath which was controlled with a temperature controller. At initial internal temperatures of 90° C., an almost immediate exotherm ensued and within 10 minutes the internal reaction temperature was 120-123° C. The exotherm was accompanied by rapid uptake of HCl. The immersion bath was raised to this temperature for 1.5-2 hours and HCl was monitored via a weigh cell (the cylinder) and a computer control system. After this period of time, virtually no more HCl uptake was apparent (approximately 32.1 g uptake). The reactor was cooled to room temperature, carefully vented to an HCl purge column, opened and the contents (68.0 g) were transferred to a glass bottle with a polyethylene screw-cap. Accurate $H_2O$, HCl and wt % organic balance was obtained on this and other samples.

The results of analysis and the chemical scheme is shown in Scheme 4 below.

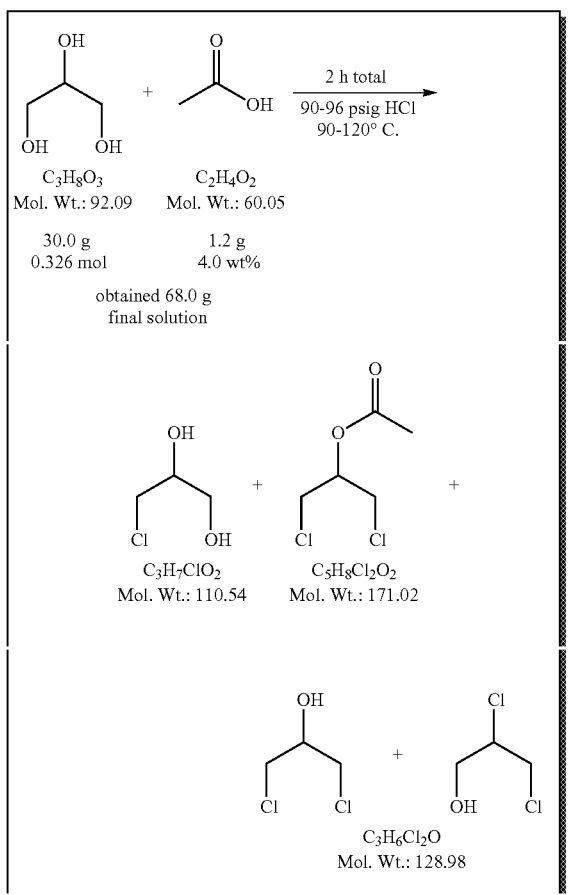

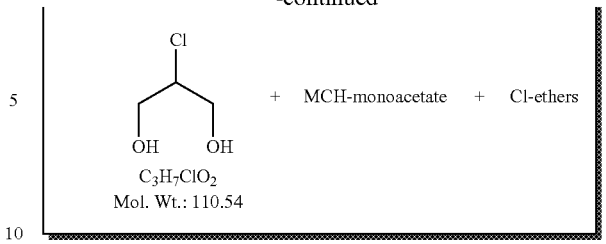

A comparison of the results of Example 42 and Comparative Example B is shown in Table II below.

TABLE II

| Component | Example 42 Pressure HCl 32.1 g HCl (Wt %) | Comparative Example B Atmospheric HCL 700 g HCl (Wt %) |
|---|---|---|
| Acetic acid | 3.6 | 0.44 |
| 1,3-DCH | 53.74 | 57.78 |
| 2,3-DCH | 1 | 1.11 |
| 3-chloro-1,2-propanediol | ND* | 9.98 |
| 2-chloro-1,3-propanediol | 1.88 | 4.03 |
| glycerol | ND | ND |
| 2-acetoxy-2,3-dichloropropane | 4.75 | 0.34 |
| 1-acetoxy-2,3-dichloropropane | 0.43 | ND |
| 1-acetoxy3-chloro-2-propanol | ND | 0.42 |
| acetoxychloropropanol | 1.25 | 0.23 |
| diacetoxychloropropane | 0.3 | ND |
| Chloroether dimers (RCl's) | 0.08 | 0.3 |
| water | 16.8 | 17.65 |
| HCl | 14.97 | 7.7 |
| Total mass balance | 99.3 | 99.98 |

*ND = not detected

Comparative Example B shows that prolonged reaction time and loss of catalysts is experienced in the atmospheric pressure example versus the superatmospheric pressure process. Also, unexpectedly, a greater conversion of monochlorohydrin to dichlorohydrin is experienced in the superatmospheric case and less chloroether (RCl) is produced. A major loss of HCl is experienced in Comparative Example B.

EXAMPLE 43

Ethylene glycol (501 mg, 8.07 mmol), 1,2-propylene glycol (519 mg, 6.82 mmol) and glacial acetic acid (102 mg, 1.715 mmol) were placed in a glass vial along with a magnetic stir bar. The vial was placed a 200 mL Hastelloy C™ pressure vessel. The pressure vessel was then pressurized with 40 psig of anhydrous HCl gas. The bottom of the vial was immersed in a water bath at 72-74° C. and stirring and pressure was maintained for 45 minutes. At the end of the reaction, the solution in the vial was transparent and clear in color. The reaction afforded 1.893 g of crude product containing water which was assayed by flame ionization detection gas chromatography. The following products were assayed based upon retention time of known commercial standards: chloroethanol (35.62 area %), 1-chloropropan-2-ol (40.47 area %), 2-chloropropan-1-ol (6.47 area %), unconverted propanediol (3.00 area %), 2-chloro-1-acetoxyethane (5.09 area %), 1-chloro-2-cetoxypropane (4.45 area %) and 2-chloro-1-acetoxypropane (0.75 area %).

EXAMPLES 44-51

The following experiments examining the effect of hydrogen chloride pressure on glycerol hydrochlorination were performed using 30 g of glycerol, 3 g. of water, 12.6 mole % acetic acid. The reaction temperature was 90° C. and the reaction time was 120 minutes. Hydrogen chloride pressure was as indicated in Table III and the selectivities to the dichlorohydrins and their acetates are as indicated.

TABLE III

| Example No. | Pressure (HCl) (psig) | 1,3-DCH Yield (mole %) | 1,3-DCH Acetate Yield (mole %) | 2,3-DCH Yield (mole %) |
|---|---|---|---|---|
| 44 | 15 | 0.2 | 0.0 | 0.0 |
| 45 | 20 | 3.2 | 0.1 | 0.1 |
| 46 | 25 | 5.0 | 0.0 | 0.1 |
| 47 | 30 | 10.2 | 0.1 | 0.2 |
| 48 | 40 | 33.5 | 0.4 | 0.6 |
| 49 | 55 | 49.4 | 0.1 | 0.9 |
| 50 | 80 | 82.0 | 2.2 | 1.4 |
| 51 | 100 | 88.7 | 2.5 | 1.5 |

EXAMPLE 52

The following example demonstrates formation of the novel composition of the present invention.

Glycerol (30 g, 326 mmols), water (3.0 g, 167 mmols) and epsilon-caprolactone (1.14 g, 10.0 mmols) were charged to a 100 ml Parr reactor, heated to 110° C. and pressurized with anhydrous hydrogen chloride to 110 psig. After 4 hours at these conditions, the reaction mixture had absorbed 34.0 grams of hydrogen chloride. The reactor contents were discharged and analyzed and found to have the following composition (excluding water and residual hydrogen chloride.

TABLE IV

| Component | Moles | Mole % |
|---|---|---|
| 1,3-Dichlorohydrin (1,3-DCH) | 0.3052 | 93.414 |
| 1-acetoxy-2,3-dichloropropane (2,3-DCH Acetate) | 0 | 0 |
| 1-Acetoxy-3-chloropropan-2-ol (1-MCH Acetate) | 0 | 0 |
| 2,3-Dichlorohydrin (2,3-DCH) | 0.0063 | 1.9197 |
| 2-acetoxy-1,3-dichloropropane (1,3-DCH Acetate) | 0 | 0 |
| 2-Monochlorohydrin (2-MCH) | 0.0122 | 3.7294 |
| Acetoxychloropropanol (MCH Acetate) | 0 | 0 |
| 1-Monochlorohydrin (1-MCH) | 0.0018 | 0.5545 |
| Diacetins (Glycerol Diacetates) | 0 | 0 |
| Diacetoxychloropropanes (MCH Diacetates) | 0.0011 | 0.3347 |
| Glycerol | 0 | 0 |
| Monacetin1 (Glycerol Acetate) | 0 | 0 |
| Monacetin2 (Glycerol Acetate) | 0 | 0 |
| 1,2,3-trichloropropane (TCP) | 0 | 0 |
| Triacetin (Glycerol Triacetate) | 0 | 0 |
| Chlorinated Diglycerols | 0.0002 | 0.0005 |

TABLE IV-continued

| Component | Moles | Mole % |
|---|---|---|
| Sum (All Organic Components) | 0.3267 | 99.9527 |
| Sum of Glycerol and Acetates | 0 | 0 |
| Sum of Monochlorohydrins and Acetates | 0.0151 | 4.6186 |
| 1,3-Dichlorohydrin and Acetate | 0.3052 | 93.414 |
| 2,3-Dichlorohydrin and Acetate | 0.0063 | 1.9197 |
| Trichloropropane | 0 | 0 |
| Chlorinated diglycerol and esters | 0.0002 | 0.0477 |

EXAMPLE 53

Use of Chlorohydrin to Prepare Epichlorohydrin

The dichlorohydrin (DCH) product prepared from Example 3 above was used in this example. This experiment used a reactive distillation apparatus consisting of a 1 liter jacketed kettle with a bottom outlet equipped at the top with a 30 tray Oldershaw section, feed point for 10% caustic/DCH feed, 6 tray Oldershaw section, aqueous return feed point and a condenser connected to a phase separator. The DCH and 10% caustic were preheated and mixed immediately prior to introduction to the system above the 30 tray Oldershaw section. Operating conditions were a pressure of 250 mm Hg, kettle temperature of 75-77° C., overhead temperature of 65-67° C. and a feed temperature of 68-76° C. The DCH feed rate and the caustic feed rate were adjusted to achieve a 10% molar excess of caustic relative to DCH. A sample of crude epichlorohydrin produced in the reaction/distillation apparatus had the following composition as analyzed by gas chromatography with a flame ionization detector (area %):

| Component | Area % |
|---|---|
| Epichlorohydrin | 99.00 |
| Glycidol | 0.04 |
| 1,3-DCH | 0.13 |
| 2,3-DCH | 0.35 |
| MCH | 0.05 |

EXAMPLES 54 AND 55 AND COMPARATIVE EXAMPLES C AND D

Hydrogen chloride was bubbled through a mixture of glycerol (30 g), water (3.0 g) and 10 mmol of catalyst at atmospheric pressure for four (4) hours at 110° C. The hydrogen chloride flow rate was controlled at 20-25 g per hour over the four (4) hour reaction period. After this time, the reaction mixture was cooled and analyzed by gas chromatography to determine the concentration of dichlorohydrins, monochlorohydrins and unreacted glycerol. Table V shows the results obtained using acetic acid, 6-hydroxyhexanoic acid, phenylacetic acid and 4-hydroxyphenylacetic acid as catalyst.

TABLE V

| | Examples | | | |
|---|---|---|---|---|
| | Comparative Example C | Example 54 | Comparative Example D | Example 55 |
| Catalyst | Acetic | 6-Hydroxyhexanoic | Phenylacetic | 4-Hydroxyphenylacetic |
| HCl Used (g) | 86.3 | 92.2 | 90 | 101 |
| Reaction Mass (g) | 50.75 | 51.78 | 48.4 | 52.5 |
| Initial Glycerol (g) | 30 | 30 | 30 | 30 |
| PRODUCTS | | | | |
| Moles DCH | 0.0502 | 0.0651 | 0.0332 | 0.0363 |

TABLE V-continued

| | Comparative Example C | Example 54 | Comparative Example D | Example 55 |
|---|---|---|---|---|
| Moles MCH | 0.2432 | 0.2365 | 0.2221 | 0.2399 |
| CONVERSIONS | | | | |
| Conversion to DCH | 15.4 | 20 | 10.2 | 11.1 |
| Conversion to MCH | 74.7 | 72.6 | 68.2 | 73.6 |
| Unconverted Glycerol | 6.9 | 8.1 | 17.5 | 17.5 |

EXAMPLES 56 AND 57

Atmospheric Pressure Hydrochlorination with Total Quantitation of Chloroacetone

Two runs of an atmospheric reaction were carried out as described below and as shown in the reaction scheme as follows:

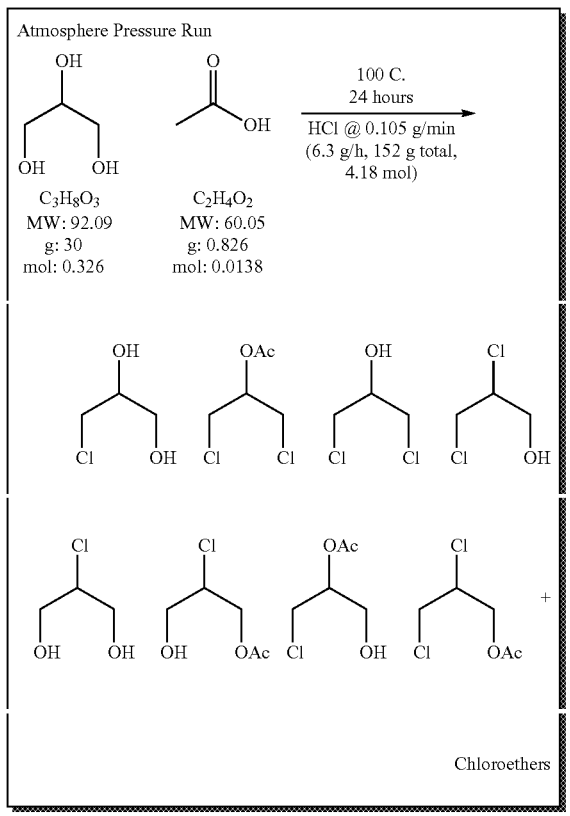

A 100 ml Parr™ reactor was equipped with an anhydrous HCl feed system, mechanical stirrer, sample port, and a vent containing a two traps in series cooled to −30° C. routed through a caustic scrubber system. The reactor was charged with 30 g of glycerol and 2.7 wt % glacial acetic acid (0.83 g). Nitrogen was purged through the reactor head space and the reactor was heated to 100° C. The nitrogen purge was switched to anhydrous HCl feed (0.105 g/min regulated by a Brooks™ 5850E Mass Flow Controller) and the reaction was allowed to progress for 24 hours. Samples were taken intermittently. A total of 161 g of HCl was added. At the end of the reaction the HCl feed was turned off, the reaction was cooled and nitrogen feed was reestablished to purge excess HCl. The reactor was disassembled and contents poured into a vial. The first trap in the vent line between the reactor and the caustic scrubber was removed, weighed and analyzed for composition. The second trap was rinsed with a known amount of water and the resulting solution was then analyzed for composition (GCMS). The results of these examples are shown in Table VI and VII below.

EXAMPLE 57

Superatmospheric Hydrochlorination of Glycerin with No Water Removal and Quantitation of Chloroacetone In this example, a super atmospheric reaction was carried out as described below and as shown in the reaction scheme as follows:

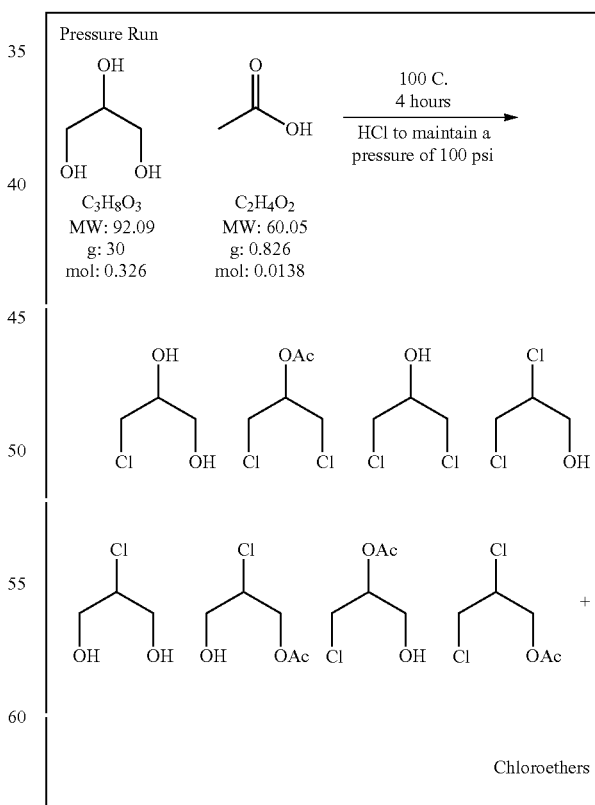

A 100 ml Parr™ reactor was charged with 30 g of glycerol and 2.7 wt % acetic acid. The reactor was purged with nitrogen at atmospheric pressure, then sealed, stirred and heated to 100° C. Anhydrous hydrochloric acid was added through a calibrated mass flow controller at a rate to maintain a constant reactor pressure of 100 psig. After 4 hours at reaction conditions, HCl feed was stopped and the reactor was cooled. The total HCl fed was 34 g. The reactor effluent was analyzed for composition (GCMS). The results of this example are shown in Table VIII below.

TABLE VI

Atmosphere Run #1: Pressure >10 psi for >50% of run time (peaked at 45 psi)

|  | Weight (g) | Cl-acetone (ppm) | Cl-acetone (gm) |
|---|---|---|---|
| Reactor Discharge | 33.45 | 228 | 0.007627 |
| Trap 1 | 9.65 | 676 | 0.006523 |
| Trap 2 | 15 | 17 | 0.000255 |
| Totals |  |  | 0.014405 | ppm Cl-acetone produced for Run #1: 334

TABLE VII

Atmosphere Run #2: Pressure <3 psi during entire course of the run

|  | Weight (g) | Cl-acetone (ppm) | Cl-acetone (gm) |
|---|---|---|---|
| Reactor Discharge | 14.46 | 390 | 0.005639 |
| Trap 1 | 28.1 | 396 | 0.011128 |
| Trap 2 | 3.5 | 6 | 0.000021 |
| Totals |  |  | 0.016788 | ppm Cl-acetone produced for Run #2: 394

TABLE VIII

Pressure Run: Pressure held at 100 psie during entire course of the run

|  | Weight (g) | Cl-acetone (ppm) | Cl-acetone (gm) |
|---|---|---|---|
| Reactor Discharge | 49.05 | 130 | 0.006377 | ppm Cl-acetone produced for Pressure Run: 130

What is claimed is:

1. A process for preparing an epoxide comprising the steps of:
   (a) contacting glycerin, an ester glycerin, or a mixture thereof with hydrogen chloride source at superatmospheric pressure in the presence of a catalyst to produce a chlorohydrin, an ester of a chlorohydrin, or a mixture thereof, said contacting step carried out without substantial removal of water; and
   (b) contacting the chlorohydrin formed in step (a) above with a base to form an epoxide; wherein the combined concentration of volatile chlorinated hydrocarbon by-products and chloroacetone is from about 0.01 ppm to less than about 2000 ppm throughout any stage of the said process;
   wherein the process is carried out at a hydrogen chloride partial pressure of from about 15 psia to about 1000 psia; and wherein the catalyst is selected from the group consisting of a carboxylic acid, an anhydride, an acid chloride, an ester, a lactone, a lactam, an amide, a metal organic compound, a metal salt, any compound convertible to a carboxylic acid under the reaction conditions of the process, and a combination thereof.

2. The process of claim 1, wherein the process is carried out in the presence of the catalyst and a co-catalyst selected from the group consisting of a chloride, a bromide and an iodide compound.

3. The process of claim 1, wherein the process is carried out in the presence of the catalyst and a co-reactant selected from the group consisting of a chloride, a bromide and an iodide compound.

4. The process of claim 3 wherein the co-reactant is a non-volatile source of ionic chloride.

5. The process of claim 4 wherein the co-reactant is sodium chloride, potassium chloride, an ionic liquid chloride salt, tetraalkylammonium chloride, n-butyl-methylimidazolium chloride, a crosslinked divinylbenzene/styrene copolymer to which an alkylarylammonium cation is covalently linked and ion paired with chloride anion, or a mixture thereof.

6. The process of claim 1, wherein the hydrogen chloride source is at least 50 mole % hydrogen chloride.

7. The process of claim 1, wherein the hydrogen chloride source is hydrogen chloride gas.

8. The process of claim 1, wherein the chlorohydrin is a dichlorohydrin, an ester of a dichlorohydrin, or a mixture thereof.

9. The process of claim 8 wherein the dichlorohydrin is 1,3-dichloropropan-2-ol; 2,3-dichloropropan-1-ol; or a mixture thereof.

10. The process of claim 1, wherein the glycerin hydrocarbon is crude glycerol or glycerin available from a renewable source.

11. The process of claim 10 wherein the crude glycerol contains less than 25 weight % water, and less than 25 weight % alkali or alkaline earth metal salts.

12. The process of claim 1, wherein the glycerin is 1,2,3-propanetriol.

13. The process of claim 1, wherein glycerin is co-fed with one or more of the following diols: 1,2-ethanediol; 1,2-propanediol, 1,3-propanediol; and butanediol positional isomers.

14. The process of claim 1, wherein the catalyst has from 1 to about 60 carbon atoms.

15. The process of claim 1, wherein the catalyst has from two to about 20 carbon atoms and has at least one functional group selected from the group consisting of an amine, an alcohol, a halogen, a sulfhydryl, an ether, an ester, and a combination thereof, wherein the functional group is attached no closer to the acid function than the alpha carbon.

16. The process of claim 1, wherein the catalyst is selected from the group consisting of acetic acid, adipic acid, propionic acid, hexanoic acid, heptanoic acid, stearic acid, butyric acid, valeric acid, 4-methylvaleric acid, phenylacetic acid, cinnamic acid, succinic acid, polyacrylic acid, polyethylene grafted with acrylic acid, epsilon-caprolactone, delta-valerolactone, gamma-butyrolactone, epsilon-caprolactam, 6-chlorohexanoic acid, 4-hydroxyphenylacetic acids, 4-aminobutyric acid, 4-dimethylaminobutyric acid, 4-trimethylammoniumbutyric acid chloride, 4-hydroxyphenylacetic acid, 4-aminophenylacetic acid, 5-chlorovaleric acid, 5-hydroxyvaleric acid, 4-hydroxybutyric acid, 4-chlorobutyric acid, 5-chloropentanoic acid, and mixtures thereof.

17. The process of claim 1, wherein the catalyst is selected from the group consisting of acetic acid, adipic acid, propionic acid, butyric acid, 4-methylvaleric acid, hexanoic acid, heptanoic acid, stearic acid, epsilon-caprolactone, gamma-butyrolactone, 6-chlorohexanoic acid, 4-aminobutyric acid, 4-dimethylaminobutyric acid, 4-trimethylammoniumbutyric acid chloride, 4-hydroxyphenylacetic acid, 4-aminophenylacetic acid, and mixtures thereof.

18. The process of claim 1, wherein the catalyst is selected from the group consisting of acetic acid, adipic acid, epsilon caprolactone, 6-chlorohexanoic acid, delta-valerolactone, 5-chloropentanoic acid, 4-chlorobutyric acid, 4-hydroxyphenylacetic acid, 4-aminophenylacetic acid, 4-aminobutyric acid, and mixtures thereof.

19. The process of claim 1, wherein the catalyst is acetic acid.

20. The process of claim 1, wherein the catalyst is caprolactone.

21. The process of claim 1, wherein the catalyst is an ester of glycerin, an ester of ethylene glycol or a compound convertible to an ester of propylene glycol under the reaction conditions; wherein said compound is selected from the group consisting of acetic acid, adipic acid, propionic acid, hexanoic acid, heptanoic acid, stearic acid, butyric acid, valeric acid, 4-methylvaleric acid, phenylacetic acid, cinnamic acid, succinic acid, benzoic acid, polyacrylic acid, polyethylene grafted with acrylic acid, epsilon caprolactone, delta-valerolactone, gamma-butyrolactone, epsilon-caprolactam, 6-chlorohexanoic acid, 4-hydroxyphenylacetic acids, 4-aminobutyric acid, 4-dimethylaminobutyric acid, 4-trimethylammoniumbutyric acid chloride, 4-hydroxyphenylacetic acid, 4-aminophenylacetic acid, 5-chlorovaleric acid, 5-hydroxyvaleric acid, 4-hydroxybutyric acid, 4-chlorobutyric acid, 5-chloropentanoic acid, and mixtures thereof.

22. The process of claim 1, wherein the catalyst is an ester selected from the group consisting of glycerin monoacetate, glycerin diacetate, glycerin distearate, 1-chloro-2,3-propanediolmonoacetate, a glycerin ester of a polycarboxylic acid, and mixtures thereof.

23. The process of claim 1, wherein the catalyst is an insoluble polymer or copolymer having carboxylic acid moieties or esters thereof.

24. The process of claim 23 wherein the insoluble polymer or copolymer is a polyester, polyacrylic acid, polyamide, polyacrylate and copolymers thereof, or mixtures thereof.

25. The process of claim 1, wherein the catalyst has a vapor pressure lower than the chlorohydrin or its azeotrope with water.

26. The process of claim 1, wherein the process is carried out at a temperature of from about 25° C. to about 300° C.

27. The process of claim 1, including the step of separating the desired chlorohydrins formed in step (a) from unreacted glycerin, undesired chlorohydrins and their esters, and catalyst prior to contacting the desired chlorohydrins with a base to form an epoxide.

28. The process of claim 27 including the step of recycling the separated unreacted glycerin, chlorohydrins and their esters, and catalyst to step (a).

29. The process of claim 27, including the step of reacting the product of step (a) with glycerin to convert the desired chlorohydrin esters to the desired chlorohydrins prior to separating the desired chlorohydrins from glycerin, undesired chlorohydrins and their esters, and catalyst.

30. The process of any one of claims 1, 27, 28 and 29, wherein the chlorohydrin in step (a) is a dichlorohydrin; and the epoxide formed is an epichlorohydrin.

31. The process of any one of claims 1, 27, 28, 29 and claim 30 wherein the base is a carbonate, bicarbonate or hydroxide of sodium, potassium, calcium, magnesium or mixtures thereof.

32. The process of claim 1, wherein the glycerin source is crude glycerol.

33. The process of claim 1, wherein the glycerin is obtained from an oleochemical material or a biomass material.

34. The process of claim 1, wherein the glycerin is a mixture of a synthetic glycerol and a glycerol obtained from an oleochemical material or a biomass material.

35. The process of claim 1, wherein the catalyst is less volatile than the desired chlorohydrin, the ester of a chlorohydrin or the mixture thereof; and wherein the catalyst has heteroatom substituents.

36. The process of claim 1, wherein the catalyst has the following Formula (a):

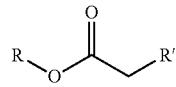

Formula (a)

wherein R' is selected from the group consisting of an amine, an alcohol, a halogen, a sulfhydryl, an ether; an alkyl, an aryl, an alkaryl group of from 1 to about 20 carbon atoms having R'; and a combination thereof; and wherein R is selected from the group consisting of hydrogen, an alkali, an alkali earth metal, a transition metal, an alkyl, an aryl, and an alkaryl group of from 1 to abut 20 carbon atoms.

37. The process of claim 1, wherein the catalyst is selected from the group consisting of lactones, esters, lactams, amides, carboxylic acids, and combinations thereof.

38. The process of claim 1, wherein the catalyst is selected from the group consisting of a caprolactone, a carboxylic acid amide, a carboxylic acid lactone, a caprolactam, and combinations thereof.

39. The process of claim 1, wherein the catalyst is selected from the group consisting of 6-hydroxyhexanoic acid, 6-chlorohexanoic acid, caprolactone, ε-caprolactam, γ-butyrolactam; γ-butyrolactone, δ-valerolactone, and ε-caprolactone; 6-aminocaproic acid; 4-aminophenylacetic acid, 4-aminobutyric acid, 4-dimethylaminobutyric acid, 4-hydroxyphenylacetic acid, 4-dimethylaminophenylacetic acid, aminophenylacetic acid, lactic acid, glycolic acid, 4-dimethylaminobutyric acid, 4-trimethylammoniumbutyric acid, and combinations thereof.

40. The process of claim 1, wherein at least some of the chlorohydrin is a dichlorohydrin.

41. The process of claim 1, wherein the dichlorohydrin is 1,3-dichloro-2-propanol or 2,3-dichloro-1-propanol.

42. The process of claim 1, wherein the volatile chlorinated hydrocarbon by-products comprise 1,2,3-trichloropropane and isomers thereof, 1,3-dichloropropene, 1,2-dichloropropene, 2,3-dichloro-1-propene, 2-chloro-2-propene-1-ol, 3-chloro-propene-1-ol; isomers thereof; or mixtures thereof.

* * * * *